(12) United States Patent
Peled et al.

(10) Patent No.: US 6,887,704 B2
(45) Date of Patent: May 3, 2005

(54) METHODS OF CONTROLLING PROLIFERATION AND DIFFERENTIATION OF STEM AND PROGENITOR CELLS

(75) Inventors: Tony Peled, Mevaseret Zion (IL); Eitan Fibach, Mevaseret Zion (IL); Avi Treves, Mevaseret Zion (IL)

(73) Assignee: Gamida Cell Ltd., Jerusalem (IL)

( * ) Notice: Subject to any disclaimer, the term of this patent is extended or adjusted under 35 U.S.C. 154(b) by 0 days.

(21) Appl. No.: 09/986,897

(22) Filed: Nov. 13, 2001

(65) Prior Publication Data

US 2002/0159981 A1 Oct. 31, 2002

Related U.S. Application Data

(63) Continuation of application No. 09/463,320, filed as application No. PCT/IL99/00444 on Aug. 17, 1999.

(51) Int. Cl.[7] .............................. C12V 5/00; C12V 5/08; C12V 5/06
(52) U.S. Cl. ...................... 435/326; 435/366; 435/372; 435/375; 435/377; 435/385; 435/384
(58) Field of Search ................................ 435/326, 366, 435/372, 375, 377, 385, 384

(56) References Cited

FOREIGN PATENT DOCUMENTS

| WO | WO 97/31647 | 9/1997 |
|---|---|---|
| WO | WO 97/33978 | 9/1997 |
| WO | WO 98/25634 A | 6/1998 |
| WO | WO 99/40783 A | 8/1999 |

OTHER PUBLICATIONS

Percival . Am .J. Clin. Nutr. 1998, vol. 67 p. 1064–1068.*
Cicuttini et al. Blood, 1992, vol. 80 , pp. 102–112.*
Piacibello et al, "Extensive Amplification and Self–Renewal of Human Primitive Hematopoietic Stem Cells from Cord Blood", Blood, 89(8):2644–2653, 1997.
Freshney, R.Ian, "Culture of Animal Cells, A Manual of Basic Technique" 3rd Ed., John Wiley & Sons, pp309–311, 327–328.
Observations on the Anemia and Neutropenia of Human Copper Deficiency, Zidar et al., American Journal of Hematology, 3: 1977, pp. 177–185.
Copper Deficiency with Pancytopenia During Total Parenteral Nutrition, Wasa et al., Journal of Parenteral and Enternal Nutrition, vol. 18, No. 3, 1994, pp 190–192.
Neutropenia Caused by Copper Deficiency: Possible Mechanism of Action, Percival, Nutrition Reviews, vol. 53, No. 3, Mar. 1995, pp 59–66.
Copper Uptake and Intracellular Distribution During Retinoic Acid–Induced Differentiation of HL–60 Cells, Bae et al., J. Nutr. Biochem., Sep. 1994, vol. 5, pp 457–461.
Retinoic Acid–Induced HL–60 Cell Differentiation is Augmented by Copper Supplementation [1–4], Bae et al., American Institute of Nutrition, Jan. 1993, pp 997–1002.
HL–60 Cells Can Be Made Copper Deficient by Incubating with Tetraethylenepentamine [1,2,3], Percival et al., American Institute of Nutrition, Aug. 25, 1992, pp 2424–2429.
Copper Deficiency and Sideroblastic Anemia Associated with Zinc Ingestion, Simon et al., American Journal of Hematology, 28, 1988, pp 181–183.
Anemia and Neutropenia in a Case of Copper Deficiency: Role of Copper in Noraml Hematopoiesis, Hirase et al., Acta Haematol, 1992, 87 pp 195–197.
Exposure of Primary Rat Hepatocytes in Long Term DMSO Culture to Selected Transition Metals Induces Hepatocyte Proliferation and Formation of Duct–Like Structure, Cable et al., Hepatology, vol. 26, No. 6, 1997, pp 1444–1457.
Extensive Amplification and Self–Renewal of Human Primitive Hematopoietic Stem Cells from Cord Blood, Piacibelio et al., Blood, vol. 89, No. 8, Apr. 16, 1997, pp. 2644–2653.
Culture of Animal Cells, Freshney, John Wiley & Sons, Third Edition, pp 309–311 and 327–328.
Metallothionein Expression and Concentrations of Cooper and Zinc are Associated with Tumor Differentiation in Hepatocellular Carcinoma, Tashiro–Itoh et al., Liver, 1997, 17, pp 300–306.
Murray, et al., *Clin. Exp. Immunol.*, 53:744–749 (1983).
Morimoto, et al., *Biochem. Int.*, 28(2):313–321 (1992).
Perrotti, et al., *Mol. Cell. Biol.*, 15(11):6075–6087 (1995).
Borthwick, et al., *J. Lab. Clin. Med.*, 95(4):575–580 (1980).
Kohroki, et al., *Leukemia Res.*, 22(5):405–412 (1998).
Lassila, et al., *Cell. Immunol.*, 122(2):319–328 (1989).
Lau, et al., *J. Biol. Chem.*, 249(18):5878–5884 (1974).
Peled, et al., *Blood*, Abstract only, 92(10 Suppl. 1 part 1–2):618A–619A (1998).
Supplementar European Search Report for EP 99 93 8494, mailing date: Jan. 8, 2004.

* cited by examiner

Primary Examiner—Christina Chan
Assistant Examiner—Michail Belyavskyi
(74) Attorney, Agent, or Firm—Mintz, Levin, Cohn, Ferris, Glovksy & Popeo, P.C.; Ivor R. Elrifi; Matthew Pavao

(57) ABSTRACT

A cell population cultured ex-vivo in a culture medium under conditions permitting cells of the cell population to proliferate and, at the same time, reducing a capacity of the cells in utilizing cooper, the cells are hence expanded yet not further differentiated as compared to ex-vivo seeded cells from which the cell population developed.

18 Claims, 22 Drawing Sheets

Fig. 26

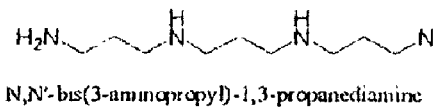
N,N'-bis(3-aminopropyl)-1,3-propanediamine

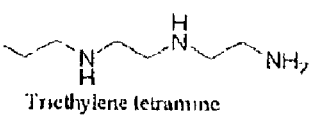
Triethylene tetramine

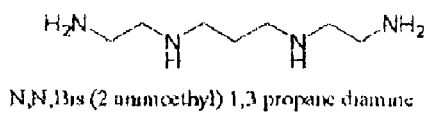
N,N,Bis (2-aminoethyl) 1,3 propane diamine

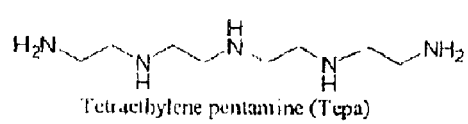
Tetraethylene pentamine (Tepa)

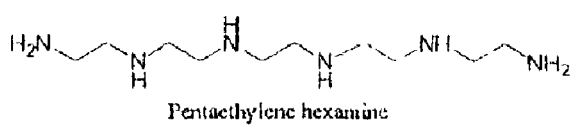
Pentaethylene hexamine

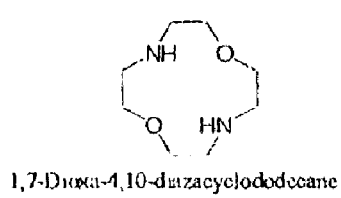
1,7-Dioxa-4,10-diazacyclododecane

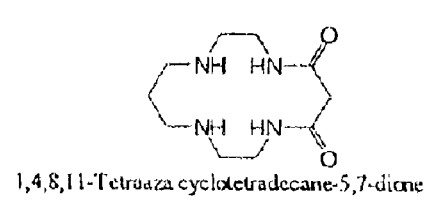
1,4,8,11-Tetraaza cyclotetradecane-5,7-dione

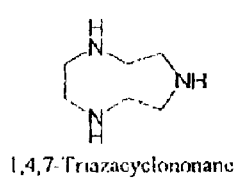
1,4,7-Triazacyclononane

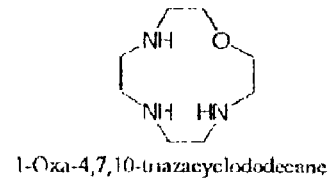
1-Oxa-4,7,10-triazacyclododecane

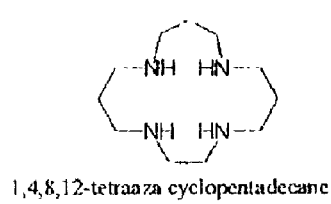
1,4,8,12-tetraaza cyclopentadecane

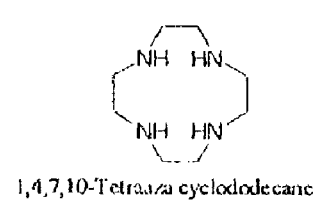
1,4,7,10-Tetraaza cyclododecane

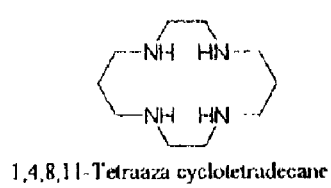
1,4,8,11-Tetraaza cyclotetradecane

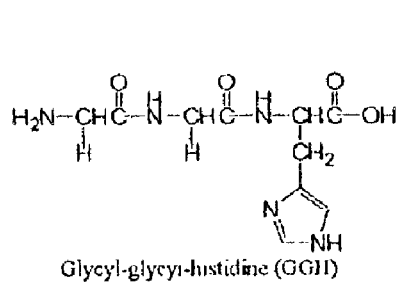
Glycyl-glycyl-histidine (GGH)

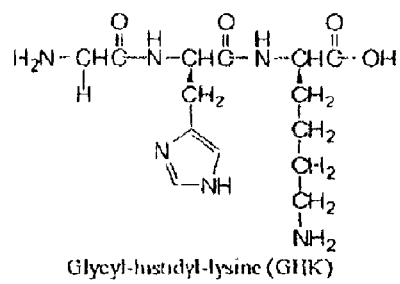
Glycyl-histidyl-lysine (GHK)

METHODS OF CONTROLLING PROLIFERATION AND DIFFERENTIATION OF STEM AND PROGENITOR CELLS

This is a continuation of U.S. patent application Ser. No. 09/463,320, filed Jan. 22, 2000, which is a 35 USC 371 filing of PCT/IL99/00444, filed Aug. 17, 1999, which claims priority from U.S. patent application Ser. No. 09/161,659, filed Sep. 29, 1998, now abandoned, which is a continuation in part of U.S. patent application Ser. No. 09/130,367, filed Aug. 7, 1998, now abandoned, which is a continuation in part of U.S. patent application Ser. No. 09/024,195, filed Feb. 17, 1998, now abandoned. In addition, PCT/IL99/00444 claims priority from PCT/US99/02664, filed Feb. 8, 1999, which claims priority from U.S. patent application Ser. Nos. 09/024,195 and 09/130,367, now abandoned.

FIELD AND BACKGROUND OF THE INVENTION

The present invention relates to methods of controlling proliferation and differentiation of stem and progenitor cells. In one aspect, the present invention relates to a method of imposing proliferation yet restricting differentiation of stem and progenitor cells by treating the cells with chelators of transitional metals, resulting in reduction in transitional metals availability. In another aspect, the present invention relates to a method of inducing differentiation of cells by treating the cells with chelators of transitional metals, resulting in increase in transitional metals availability to the cells. In still another aspect, the present invention relates to assays for determining whether a specific chelator of transitional metals will restrict or induce differentiation.

Cell differentiation and proliferation

Normal production of blood cells (hematopoiesis) and of other cell types involves the processes of proliferation and differentiation which are tightly coupled. In most hematopoietic cells following division the daughter cells undergo a series of progressive changes which eventually culminate in fully differentiated (mature), functional blood cells, which in most part are devoid of proliferative potential. Thus, the process of differentiation limits, and eventually halts cell division. Only in a small minority of the hematopoietic cells, known as stem cells, cell division may result in progeny which are similar or identical to their parental cells. This type of cell division, known as self-renewal, is an inherent property of stem cells and helps to maintain a small pool of stem cells in their most undifferentiated state. Some stem cells lose their self-renewal capacity and following cell division differentiate into various types of lineage committed progenitors which finally give rise to mature cells. While the latter provide the functional capacity of the blood cell system, the stem cells are responsible for the maintaining of hematopoiesis throughout life despite a continuous loss of the more differentiated cells through apoptosis (programmed cell death) and/or active removal of aging mature cells by the reticuloendothelial system. It will be appreciated that in one way or another these processes characterize all other cell lineages of multicellular organisms, because replenishment of dead cells occurs during the life cycle of such organisms.

Normal hematopoiesis is coordinated by a variety of regulators which include glycoproteins such as the colony stimulating factors (CSF), as well as small molecules such as the retinoids. They regulate the survival (e.g., by inhibiting apoptosis), proliferation and differentiation of progenitor and precursor cells and the activation state of mature cells.

In acute leukemia, for example, there is a block in cell differentiation. As a results, the leukemic cells maintain their proliferative potential. Leukemic cells do not respond normally to the various regulators (54). Thus, cells obtained from patients with acute mycloid leukemia develop in culture, in response to stimulation by colony stimulating factor (CSF), small colonies of undifferentiated cells, as compared to large colonies of granulocytes and macrophages, which develop following cloning normal hematopoietic cells.

As further detailed below, expansion of the stem cell and other defined lympho-hematopoietic cell subpopulations by ex-vivo culturing could have important clinical applications.

A variety of protocols have been suggested and experimented for enrichment of such populations. The main experimental strategies employed include incubation of mononuclear cells with or without selection of $CD_{34}^+$ (8); with different cocktails of early and late growth factors (17); with or without serum (7); in stationary cultures, rapid medium exchanged cultures (18) or under continuous perfusion (bioreactors) (6); and with or without established stromal cell layer (19).

Although a significant expansion of intermediate and late progenitors was often obtained during 7–14 days ex-vivo cultures, the magnitude of early hematopoietic ($CD_{34}^+$ $CD_{38}^-$) stem cells with high proliferative potential, usually declined (6, 20–22).

Thus, these cultures do not result in true stem cell expansion, but rather in proliferation and differentiation of the stem cells into pre-progenitor cells, accompanied by depletion of the primitive stem cell pool.

In order to achieve maximal ex-vivo expansion of stem cells the following conditions should be fulfilled: (i) differentiation should be reversibly inhibited or delayed and (ii) self-renewal should be maximally prolonged.

Similarly, following cell expansion, it is important to have methods to induce differentiation of the expanded cell population, so as to covert the expanded cell population to mature functional cells or tissue.

Role of copper in cell differentiation:

The possible involvement of Copper in hematopoietic cell development could be inferred from the following findings:

Clinical symptoms in Copper deficiency: Copper deficiency can result from hereditary defects, such as Menkes syndrome or Celiac disease, or from acquired conditions. The latter is typically associated with malnourishment. It may be caused by Copper non-supplemented total parenteral nutrition (e.g., following intestinal resection), by consumption of high levels of Zinc, which interferes with Copper utilization, in underweight and/or cow milk (poor source of Copper) fed new-borns, which may result in severe cases in Shwanchman syndrome. Unbalanced treatment with Copper chelators in Copper overload cases such as in Wilson's disease may also lead to Copper deficiency.

The clinical symptoms of Copper deficiency may include impairment of growth, brain development, bone strength and morphology, myocardial contractility, cholesterol and glucose metabolism, host defence (immune) mechanisms and more.

Of particular relevance to this study is the fact that Copper deficiency is often associated with hematological abnormalities, including anemia, neutropenia and thrombocytopenia. All these pathological manifestations are unresponsive to iron therapy, but are rapidly reversed following Copper supplementation (27–28).

The mechanism by which Copper deficiency leads to neutropenia is unknown. Among the possible causes, either alone or in combination, are: (i) early death of progenitor cells in the bone marrow (BM); (ii) impaired formation of neutrophils from progenitor cells in the BM; (iii) decrease in cellular maturation rate in the BM; (iv) impaired release of neutrophils from the BM to the circulation; (v) enhanced elimination rate of circulating neutrophils.

Examination of the BM of neutropenic Copper-deficient patients demonstrates the absence of mature cells ("maturation arrest"). It has been shown that cells derived from such BM did not form colonies in semi-solid medium containing Copper deficient serum, but retained the potential for normal colony growth in Copper containing serum. These results indicate the presence of intact progenitors in the patient's BM, and suggest that the block in development occurs distal to the progenitor stage (29–30).

The effect of Copper in cell lines: The effect of Copper was also studied in-vitro established cell lines (31–34). One such line (HL-60) was derived from a patient with acute promyelocytic leukemia. These cells, that have the characteristics of myeloblasts and promyelocytes, can grow indefinitely in culture. Upon addition of various agents, such as retinoic acid (RA), to the culture medium, the cells undergo differentiation, which results in cells which demonstrate some, but not all, features of mature granulocytes.

The study of Copper status in these cells has shown that although the cytosolic Copper content per cell was not significantly different in RA-treated cells compared to untreated cells, the Copper content per protein content was doubled. This is due to the fact that RA-treated cells have about half the protein content as compared to their untreated counterpart. Using $^{67}Cu$, it has been shown that the rate of Copper uptake was significantly faster during the two first days of RA treatment, but not at later times. The intracellular distribution of $^{67}Cu$ was found predominantly in high molecular weight (MW) fractions (>100 kD) and a lower MW fraction of about 20 kD), with a higher proportion of Copper present in the high MW fractions in RA-treated cells.

Addition of excess Copper to regular serum-supplemented growth medium modestly increased RA-induced differentiation. Although RA-treated HL-60 cells do not necessarily represent normal cell development, these results point to the possibility that neutrophilic differentiation may require Copper.

In other experiments it has been shown that HL-60 cells can be made Copper deficient by treatment with Copper chelators, and that following such treatment their viability and growth rate were unaffected.

Although all these phenomena have been attributed to Copper, it has been reported that some clinical and biological effects are shared by Copper and other transition metals:

For example, clinical symptoms similar to those observed in Copper-deficiency could also be observed following consumption of high levels of Zinc (40–42), which has been known to interfere with Copper utilization (e.g., 43).

In a study of human hepatocellular carcinoma it was found that the concentrations of both Copper and Zinc in the tumor tissue decreased with the degree of histological differentiation (44).

In another study it was shown that addition of Copper, Zinc and Ferrum to primary cultures of rat hepatocytes induced cell replication and formation of duct-like structures. The cells lining the ducts became morphologically and biochemically characteristic of bile duct cells (45).

Various transition metals are known to influence the production and activities of many enzymes and transcription factors associated with differentiation. Examples include the Cu/Zn containing superoxide dismutase (46); the metallothioneins and their transcription regulating factors (e.g., MTF-1) (47–49); the 70 kDa heat shock protein (hsp70) (50); the p62 protein which associates with the ras-GTPase activating protein during keratinocyte differentiation (51); a neutral sphingomyelinase which is activated during induced differentiation of HL-60 cells (52); and the bovine lens leucine aminopeptidase (53).

Oligopeptides, either natural or synthetic, can bind Copper too. Thus, glycyl-L-histidyl-L-lysine-$Cu^{2+}$ (GHL-Cu) is a tripeptide-Copper complex that was isolated from human plasma. It has been shown to have, in nanomolar concentrations, a variety of biological effects both in-vitro and in-vivo: It was first described as a growth factor for a variety of differentiated cells (55). Subsequent data from various groups indicated that it exhibited several properties of a potent activator of the wound healing process. It was a potent chemotactic agent for monocytes/macrophages and mast cells (56–57). It stimulated nerve tissue regeneration (58) and was reported to trigger the angiogenesis process in-vivo (59). It stimulated collagen synthesis in several fibroblast strains (60). It accelerated wound closure when injected into superficial wounds in animals (61–62) and accumulation of collagen and dermatan sulfate proteoglycans (63). It also exerted metabolic effects, such as inhibition of lipid peroxidation by feritin (64). GHL-metal ions combinations were shown to promote monolayer formation and cellular adhesiveness in tumorigenic hepatoma ($HTC_4$) cells in culture, resulting in marked enhancement of cell survival and growth under basal (growth limiting) conditions (65). The mode of action of GHL is unknown. It has been reported that GHL forms chelates with Copper and iron in human plasma and in buffered solution at physiological pH.

While reducing the present invention to practice, it was found that a series of chemical agents that bind (chelate) transition metals, Copper in particular, can inhibit (delay) the process of differentiation of stem cells as well as intermediate and late progenitor cells and thereby stimulate and prolong the phase of active cell proliferation and expansion ex-vivo. This newly discovered effect of Copper and other transition metals depletion (either partial or complete depletion) was used for maximizing the ex-vivo expansion of various types of cells as further detailed hereinunder. However, it was also found, while reducing the present invention to practice, that a series of other transition metal chelators, Copper chelators in particular, can induce the process of differentiation in cells, e.g., both normal and leukemic hematopoietic cells ex-vivo.

SUMMARY OF THE INVENTION

It is one object of the present invention to provide a method of expanding a population of cells, while at the same time inhibiting differentiation of the cells.

It is another object of the present invention to provide a method of hematopoietic cells transplantation.

It is still another object of the present invention to provide a method of genetically modifying stem cells with an exogene.

It is yet another object of the present invention to provide a method of adoptive immunotherapy.

It is an additional object of the present invention to provide a method of mobilization of bone marrow stem cells into the peripheral blood of a donor for harvesting the cells.

It is yet an additional object of the present invention to provide a method of decelerating maturation/differentiation of erythroid precursor cells for the treatment of β-hemoglobinopathic patients.

It is still an additional object of the present invention to provide a method of preservation of stem cells.

It is a further object of the present invention to provide stem cell collection bags.

It is still a further object of the present invention to provide assays of determining whether a transition metal chelator which binds copper causes inhibition or induction of differentiation.

It is yet a further object of the present invention to provide a method of inducing differentiation in a population of cells.

It is another object of the present invention to provide a method of inducing terminal differentiation in acute leukemic cells.

It is still another object of the present invention to provide a method of induction of differentiation of non-leukemic hematopoietic progenitor cells.

It is still another object of the present invention to provide a method of ex-vivo differentiation of normal stem cells into lineage committed progenitor cells.

It is an additional object of the present invention to provide a method of ex-vivo differentiation of stem cells into dendritic cell committed progenitors.

It is still an additional object of the present invention to provide a pharmaceutical composition for inducing differentiation in a population of cells.

Thus, according to one aspect of the present invention there is provided a method of expanding a population of cells, while at the same time inhibiting differentiation of the cells, the method comprising the step of providing the cells with conditions for cell proliferation and, at the same time, for reducing a capacity of the cells in utilizing copper.

According to further features in preferred embodiments of the invention described below, the cells are in-vivo, where the conditions for cell proliferation are naturally provided, whereas reducing the capacity of the cells in utilizing transition metals is effected by administering a transition metal chelator which binds copper.

According to still further features in the described preferred embodiments reducing the capacity of the cells in utilizing copper is further effected by administering Zinc.

According to still further features in the described preferred embodiments the cells are in-vivo, where the conditions for cell proliferation are naturally provided, whereas reducing the capacity of the cells in utilizing copper is effected by administering Zinc.

According to still further features in the described preferred embodiments reducing the capacity of the cells in utilizing copper is further effected by administering a transition metal chelator which binds copper.

According to still further features in the described preferred embodiments reducing the capacity of the cells in utilizing copper is effected by a transition metal chelator that binds copper.

According to still further features in the described preferred embodiments the transition metal chelator is selected from the group consisting of polyamine chelating agents, ethylendiamine, diethylenetriamine, triethylenetetramine, triethylenediamine, tetraethylenepentamine, aminoethylethanolamine, aminoethylpiperazine, pentaethylenehexamine, triethylenetetramine-hydrochloride, tetraethylenepentamine-hydrochloride, pentaethylenehexamine-hydrochloride, tetraethylpentamine, captopril, penicilamine, N,N'-bis(3-aminopropyl)-1,3-propanediamine, N,N,Bis(2 animoethyl) 1,3 propane diamine, 1,7-dioxa-4,10-diazacyclododecane, 1,4,8,11-tetraaza cyclotetradecane-5,7-dione, 1,4,7-triazacyclononane trihydrochloride, 1-oxa-4,7,10-triazacyclododecane, 1,4,8,12-tetraaza cyclopentadecane, 1,4,7,10-tetraaza cyclododecane.

According to still further features in the described preferred embodiments the cells are ex-vivo.

According to still further features in the described preferred embodiments providing the cells with the conditions for cell proliferation include providing the cells with nutrients and with cytokines.

According to still further features in the described preferred embodiments the cytokines are early acting cytokines.

According to still further features in the described preferred embodiments the early acting cytokines are selected from the group consisting of stem cell factor, FLT3 ligand, interleukin-6, thrombopoietin and interleukin-3.

According to still further features in the described preferred embodiments the cytokines are late acting cytokines.

According to still further features in the described preferred embodiments the late acting cytokines are selected from the group consisting of granulocyte colony stimulating factor, granulocyte/macrophage colony stimulating factor and erythropoietin.

According to still further features in the described preferred embodiments the cells are selected from the group consisting of hematopoietic cells, neural cells and oligodendrocyte cells, skin cells, hepatic cells, embryonic stem cells, plant cells, muscle cells, bone cells, mesenchymal cells, pancreatic cells, chondrocytes and stroma cells.

According to still further features in the described preferred embodiments the cells are derived from a source selected from the group consisting of bone marrow, peripheral blood and neonatal umbilical cord blood.

According to still further features in the described preferred embodiments the cells are enriched for hematopoietic $CD_{34}^+$ cells.

According to still further features in the described preferred embodiments the cells are selected from the group consisting of non-differentiated stem cells and committed progenitor cells.

According to another aspect of the present invention there is provided a method of hematopoietic cells transplantation comprising the steps of (a) obtaining hematopoietic cells to be transplanted from a donor; (b) providing the cells ex-vivo with conditions for cell proliferation and, at the same time, for reducing a capacity of the cells in utilizing cooper, thereby expanding a population of the cells, while at the same time, inhibiting differentiation of the cells; and (c) transplanting the cells to a patient.

According to further features in preferred embodiments of the invention described below, the donor and the patient are a single individual.

According to still further features in the described preferred embodiments obtaining the hematopoietic cells is from a source selected from the group consisting of peripheral blood, bone marrow, neonatal umbilical cord blood and embryonic stem cells.

According to still further features in the described preferred embodiments obtaining the hematopoietic cells further includes enriching the cells for stem cells.

According to still further features in the described preferred embodiments obtaining the hematopoietic cells further includes enriching the cells for progenitor cells.

According to yet another aspect of the present invention there is provided a method of genetically modifying stem cells with an exogene comprising the steps of (a) obtaining stem cells to be genetically modified; (b) providing the cells ex-vivo with conditions for cell proliferation and, at the same time, for reducing a capacity of the cells in utilizing cooper, thereby expanding a population of the cells, while at the same time, inhibiting differentiation of the cells; and (c) genetically modifying the cells with the exogene. Preferably, genetically modifying is effected by a vector including the exogene.

According to still another aspect of the present invention there is provided a method of adoptive immunotherapy comprising the steps of (a) obtaining progenitor hematopoietic cells from a patient; (b) providing the cells ex-vivo with conditions for cell proliferation and, at the same time, for reducing a capacity of the cells in utilizing cooper, thereby expanding a population of the cells, while at the same time, inhibiting differentiation of the cells; and (c) transplanting the cells to the patient.

According to an additional aspect of the present invention there is provided a method of mobilization of bone marrow stem cells into the peripheral blood of a donor for harvesting the cells comprising the step of (a) administering to the donor an agent for reducing a capacity of the cells in utilizing cooper, thereby expanding a population of stem cells, while at the same time, inhibiting differentiation of the stem cells; and (b) harvesting the cells by leukapheresis.

According to further features in preferred embodiments of the invention described below, the method further comprising the step of administering the donor a cytokine.

According to still further features in the described preferred embodiments the method further comprising the step of administering the donor a cytokine.

According to still further features in the described preferred embodiments the cytokine is selected from the group consisting of stem cell factor, FLT3 ligand, interleukin-6, thrombopoietin, interleukin-3, granulocyte colony stimulating factor, granulocyte/macrophage colony stimulating factor and erythropoietin.

According to yet an additional aspect of the present invention there is provided a method of decelerating maturation/differentiation of erythroid precursor cells for the treatment of β-hemoglobinopathic patients comprising the step of administering to the patient an agent for reducing a capacity of the cells in utilizing cooper, thereby expanding a population of stem cells, while at the same time, inhibiting differentiation of the stem cells, such that upon natural removal of the agent from the body, the stem cells undergo accelerated maturation resulting in elevated production of fetal hemoglobin.

According to still an additional aspect of the present invention there is provided a therapeutical ex-vivo cultured cell preparation comprising ex-vivo cells propagated in the presence of an agent, the agent reducing a capacity of the cells in utilizing cooper, thereby expanding a population of the cells, while at the same time, inhibiting differentiation of the cells.

According to still further features in the described preferred embodiments the agent is selected from the group consisting of a transition metal chelator and Zinc.

According to a further aspect of the present invention there is provided a method of preservation of stem cells comprising the step of handling the stem cell in at least one of the steps selected from the group consisting of harvest, isolation and storage, in a presence of a transition metal chelator which binds copper and/or Zinc.

According to yet a further aspect of the present invention there is provided stem cell collection bags, separation and washing buffers supplemented with an effective amount or concentration of a transition metal chelator which binds copper and/or with Zinc, which inhibits cell differentiation.

According to still a further aspect of the present invention there is provided an assay of determining whether a transition metal chelator which binds copper causes inhibition or induction of differentiation, the assay comprising the step of culturing a population of stem or progenitor cells or cells of a substantially non-differentiated cell line, in the presence of the transition metal chelator and monitoring differentiation of the cells, wherein if differentiation is increased as is compared to non-treated cells, the transition metal chelator induces differentiation, whereas if differentiation is decreased or as compared to non-treated cells, or if differentiation is absent altogether, the transition metal chelator inhibits differentiation.

According to another aspect of the present invention there is provided an assay of determining whether a transition metal chelator which binds copper causes inhibition or induction of differentiation, the assay comprising the step of culturing a population of cells in the presence of the transition metal chelator and monitoring copper content of the cells, wherein if the copper content of the cells is increased as is compared to non-treated cells, the transition metal chelator induces differentiation, whereas if copper content is decreased as compared to non-treated cells the transition metal chelator inhibits differentiation.

According to yet another aspect of the present invention there is provided a method of inducing differentiation in a population of cells, the method comprising the step of providing the cells with a transition metal chelator which binds copper and which is effective in inducing cell differentiation.

According to further features in preferred embodiments of the invention described below, the cells are in-vivo.

According to still further features in the described preferred embodiments the cells are grown ex-vivo.

According to still further features in the described preferred embodiments the cells are hematopoietic cells.

According to still further features in the described preferred embodiments the cells are selected from the group consisting of normal cells and cancer cells.

According to still further features in the described preferred embodiments the transition metal chelator is a tripeptide.

According to still further features in the described preferred embodiments the transition metal chelator is selected from the group consisting of GGH, GHL and 1,4,8,11-tetraaza cyclotetradecane.

According to still further features in the described preferred embodiments the transition metal chelator is GGH.

According to still further features in the described preferred embodiments the transition metal chelator is a peptide or a peptide analog.

According to still further features in the described preferred embodiments the transition metal chelator includes a peptide sequence.

According to still further features in the described preferred embodiments the peptide sequence is selected from the group consisting of SEQ ID NOS:1 and 2.

According to still further features in the described preferred embodiments the cells are selected from the group consisting of hematopoietic stem or progenitor cells, neural stem or progenitor cells, oligodendrocyte stem or progenitor cells, skin stem or progenitor cells, hepatic stem or progenitor cells, muscle stem or progenitor cells, bone stem or progenitor cells, mesenchymal stem or progenitor cells, pancreatic stem or progenitor cells, stem or progenitor chondrocytes, stroma stem or progenitor cells, embryonic stem cells and cultured expanded stem or progenitor cells.

According to still further features in the described preferred embodiments the cells are derived from a source selected from the group consisting of bone marrow, peripheral blood and neonatal umbilical cord blood.

According to still further features in the described preferred embodiments the cells are enriched for hematopoietic $CD_{34}$+ cells.

According to still further features in the described preferred embodiments the cells are selected from the group consisting of non-differentiated stem cells and committed progenitor cells.

According to still another aspect of the present invention there is provided a method of inducing terminal differentiation in acute leukemic cells, the method comprising the step of providing the cells with a transition metal chelator which binds copper and which is effective in inducing cell differentiation.

According to an additional aspect of the present invention there is provided a method of induction of differentiation of non-leukemic hematopoietic progenitor cells, the method comprising the step of providing the cells with a transition metal chelator which binds copper and which is effective in inducing cell differentiation.

According to still further features in the described preferred embodiments the cells are selected from the group consisting of in-vivo and ex-vivo cells.

According to yet an additional aspect of the present invention there is provided a method of ex-vivo differentiation of normal stem cells into lineage committed progenitor cells, the method comprising the step of providing the cells with a transition metal chelator which binds copper and which is effective in inducing cell differentiation.

According to still an additional aspect of the present invention there is provided a method of ex-vivo differentiation of stem cells into dendritic cell committed progenitors, the method comprising the step of providing the cells with a transition metal chelator which binds copper and which is effective in inducing cell differentiation.

According to a further aspect of the present invention there is provided a pharmaceutical composition for inducing differentiation in a population of cells, comprising transition metal chelator which binds copper and which is effective in inducing cell differentiation, and a pharmaceutically acceptable carrier.

The present invention successfully addresses the shortcomings of the presently known configurations by providing a method of propagating cells, yet delaying their differentiation by Copper deficiency. The present invention further successfully addresses the shortcomings of the presently known configurations by providing new means of inducing cell differentiation.

Additional features and advantages of the method according to the present invention are described hereinunder.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 26 shows the chemical structure of transition metal chelators used in an assay according to the present invention, which can be used to determine the potential of any chelator to arrest or induce cell differentiation.

DESCRIPTION OF THE PREFERRED EMBODIMENTS

Figure 1:
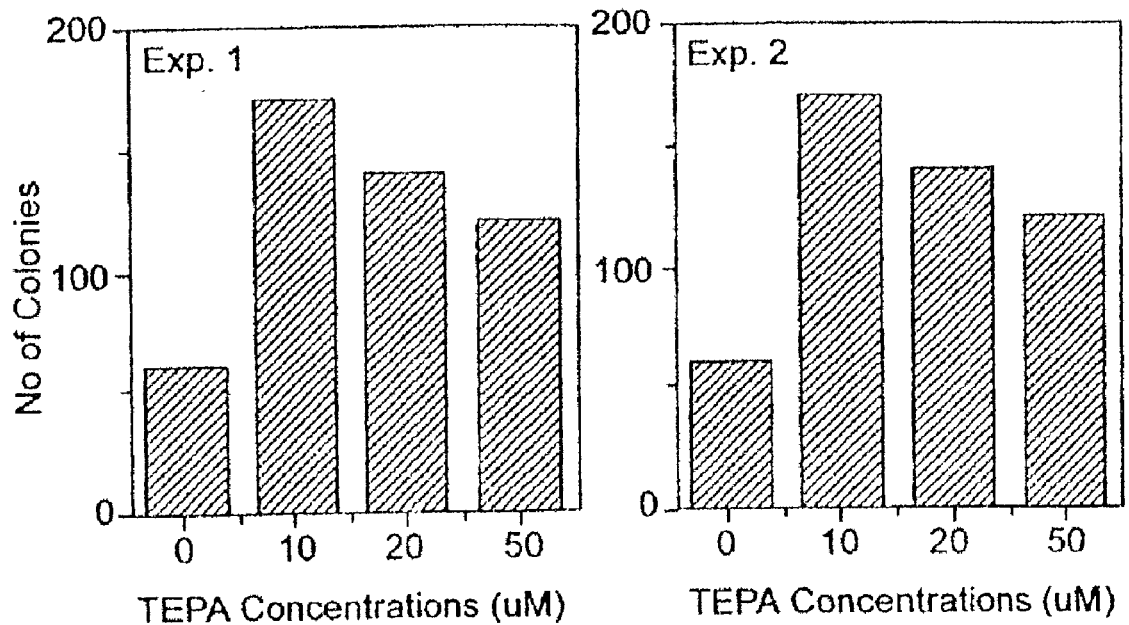
FIG. 1 shows the short-term effect of TEPA on the clonlogenic potential of $CD_{34}$ cells. Cord blood-derived $CD_{34}$ cells were plated in liquid culture, at $3 \times 10^4$ cell/ml, in the presence of low dose cytokines: FLT3—5 ng/ml, SCF—10 ng/ml, IL-6—10 ng/ml, with or without different concentrations of TEPA. On day 7, aliquots of 0.1 ml were assayed for colony forming cells by cloning the cells in semi-solid medium and scoring colonies after 14 days. Results of two independent experiments are presented.

The present invention is of methods of controlling proliferation and/or modulating differentiation of stem and progenitor cells, which can be used to provide a therapeutical ex-vivo cultured cell preparation which includes a large population of cells, in which differentiation was inhibited while cell expansion propagated, and which can alternatively be used to induce cell differentiation. Specifically, the present invention can be used, on one hand, to provide expanded populations of stem cells, as well as progenitor cells, which can be used for, for example, hematopoietic cell transplantations, or the generation of stem or progenitor cells suitable for genetic manipulations, which may be used for gene therapy, and new treatment means for diseases, such as, but not limited to, β-hemoglobinopathia, or alternatively, the present invention can be used to provide a large population of differentiated cells, which can be used, for example, for cell transplantations and for genetic manipulations, which may be used for gene therapy.

Thus, the present invention relates to a method of controlling proliferation and differentiation of stem and progenitor cells. More particularly, in one aspect, the present invention relates to a method of imposing proliferation yet restricting differentiation of stem and progenitor cells, whereas, in another aspect, the present invention relates to a method of inducing differentiation of stem and progenitor cells by apparently modifying the availability of transition metals, Copper in particular. In both case, the present invention is effected by modifying (decreasing or increasing) the availability of transition metals, Copper in particular, to cells undergoing cell expansion according to the first aspect of the invention or to cells undergoing differentiation, according to the second aspect of the present invention.

The principles and operation of the methods according to the present invention may be better understood with reference to the drawings and accompanying descriptions and examples.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In the course of the present study it was found that a series of chemical agents that bind (chelate) Copper and other transition metals, or that interfere with Copper metabolism can reversibly inhibit (delay) the process of differentiation of stem cells as well as intermediate and late progenitor cells and thereby stimulate and prolong the phase of active cell proliferation.

This newly discovered effect of transition metal depletion was utilized for maximizing the ex-vivo expansion of various types of cells including hematopoietic cells, hepatocytes and embryonic stem cells. Such ex-vivo expanded cells can be applied in several clinical situations. The following lists few.

Hematopoietic cell transplantation: Transplantation of hematopoietic cells has become the treatment of choice for a variety of inherited or malignant diseases. While early transplantation procedures utilized the entire bone marrow (BM) population, recently, more defined populations, enriched for stem cells ($CD_{34}^+$ cells) have been used (1).

In addition to the marrow, such cells could be derived from other sources such as peripheral blood (PB) and neonatal umbilical cord blood (CB) (2). Compared to BM, transplantation with PB cells shortens the period of pancytopenia and reduces the risks of infection and bleeding (3–5).

An additional advantage of using PB for transplantation is its accessibility. The limiting factor for PB transplantation is the low number of circulating pluripotent stem/progenitor cells.

To obtain enough PB-derived stem cells for transplantation, these cells are "harvested" by repeated leukapheresis following their mobilization from the marrow into the circulation by treatment with chemotherapy and cytokines (3–4). Such treatment is obviously not suitable for normal donors.

The use of ex-vivo expended stem cells for transplantation has the following advantages (2, 6–7).

It reduces the volume of blood required for reconstitution of an adult hematopoietic system and may obviate the need for mobilization and leukapheresis (3).

It enables storage of small number of PB or CB stem cells for potential future use.

In the case of autologous transplantation of patients with malignancies, contaminating tumor cells in autologous infusion often contribute to the recurrence of the disease (3). Selecting and expanding $CD_{34}^+$ stem cells will reduce the load of tumor cells in the final transplant.

The cultures provide a significant depletion of T lymphocytes, which may be useful in the allogeneic transplant setting for reducing graft-versus-host disease.

Clinical studies have indicated that transplantation of ex-vivo expanded cells derived from a small number of PB $CD_{34}^+$ cells can restore hematopoiesis in patients treated with high doses of chemotherapy, although the results do not allow yet firm conclusion about the long term in-vivo hematopoietic capabilities of these cultured cells (3–4).

For successful transplantation, shortening of the duration of the cytopenic phase, as well as long-term engraftment, is crucial. Inclusion of intermediate and late progenitor cells in the transplant could accelerate the production of donor-derived mature cells and shortens the cytopenic phase. It is important, therefore, that ex-vivo expanded cells will include, in addition to stem cells, more differentiated progenitors in order to optimize short-term recovery and long term restoration of hematopoiesis. Expansion of intermediate and late progenitor cells, especially those committed to the neutrophilic and megakayocytic lineages, concomitant with expansion of stem cells, should serve this purpose (8).

Such cultures may be useful not only in restoring hematopoiesis in completely bone marrow ablated patients but also as supportive measure for shortening bone marrow recovery following conventional radio- or chemo-therapies.

Prenatal diagnosis of genetic defects in scarce cells: Prenatal diagnosis involved the collection of embryonic cells from a pregnant woman and analysis thereof for genetic defects. A preferred, non-invasive, way of collecting embryonic cells involves separation of embryonic nucleated red blood cell precursors that infiltrated into the maternal blood circulation. However, being very scarce, such cells should undergo cell expansion prior to analysis. The present invention therefore offers means to expand embryonic cells for prenatal diagnosis.

Gene therapy: For a successful long-term gene therapy a high frequency of genetically modified stem cells that have integrated the transgene into their genome is an obligatory requirement. In the BM tissue, while the majority of the cells are cycling progenitors and precursors, the stem cells constitute only a small fraction of the cell population and most of them are in a quiescent, non-cycling state. Viral-based (e.g., retroviral) vectors require active cell division for integration of the transgene into the host genome. For these reasons gene transfer into fresh BM stem cells is very inefficient. The ability to expand a purified population of stem cells and to regulate their cell division ex-vivo would permit increased probability of their genetic modification (9).

Adoptive immunotherapy: Ex-vivo-expanded, defined lymphoid subpopulations have been studied and used for adoptive immunotherapy of various malignancies, immunodeficiency, viral and genetic diseases (10–12).

The treatment enhances the required immune response or replaces deficient functions. This approach was pioneered clinically by Rosenberg et al. (13) using a large number of autologous ex-vivo expanded non-specific killer T cells, and subsequently ex-vivo expanded specific tumor infiltrating lymphocytes.

It was also shown that functionally active antigen-presenting cells can be grown from a starting population of $CD_{34}^+$ PB cells in cytokine-supported cultures. These cells can present soluble protein antigens to autologous T cells in-vitro and, thus, offer new prospects for the immunotherapy of minimal residual disease after high dose chemotherapy. Ex-vivo expansion of antigen-presenting dendritic cells was also studied (14–16).

Ex-vivo expansion of non-hematopoietic stem and progenitor cells: For example, ex-vivo expansion of neural stem cells or oligodendrocyte progenitors, etc.

Myelin disorders form an important group of human neurological diseases that are as yet incurable. Progress in animal models, particularly in transplanting cells of the oligodendrocyte lineage, has resulted in significant focal remyelination and physiological evidence of restoration of function (36). Future therapies could involve both transplantation and promotion of endogenous repair, and the two approaches could be combined with ex-vivo manipulation of the donor tissue.

U.S. Pat. No. 5,486,359 teaches isolated human mesenchymal stem cells which can differentiate into more than one tissue type (e.g. bone, cartilage, muscle or marrow stroma) and a method for isolating, purifying, and culturally expanding human mesenchymal stem cells.

U.S. Pat. No. 5,736,396 teaches methods for in-vitro or ex-vivo lineage-directed induction of isolated, culture expanded human mesenchymal stem cells comprising the steps of contacting the mesenchymal stem cells with a bioactive factor effective to induce differentiation thereof into a lineage of choice. Further disclosed is a method which also includes introducing such culturally expanded lineage-induced mesenchymal stem cells into a host from which they have originated for purposes of mesenchymal tissue regeneration or repair.

U.S. Pat. No. 4,642,120 teaches compositions for repairing defects of cartilage and bones. These are provided in gel form either as such, or embedded in natural or artificial bones. The gel comprises certain types of cells. These may be committed embryonal chondocytes or any kind of mesenchyme originated cells which potentially can be converted to cartilage cells, generally by the influence of chondrogenic inducing factors, in combination with fibrinogen, antiprotease and thrombin.

U.S. Pat. No. 5,654,186 teaches that blood-borne mesenchymal cells proliferate in culture, and in-vivo, as demonstrated in animal models, are capable of migrating into wound sites from the blood to form skin.

U.S. Pat. No. 5,716,411 teaches to a method of skin regeneration of a wound or burn in an animal or human. This method comprises the steps of initially covering the wound with a collagen glycosaminoglycan matrix, allowing infiltration of the grafted GC matrix by mesenchymal cells and blood vessels from healthy underlying tissue and applying a cultured epithelial autograft sheet grown from epidermal cells taken from the animal or human at a wound-free site on the animal's or human's body surface. The resulting graft has excellent take rates and has the appearance, growth, maturation and differentiation of normal skin.

U.S. Pat. No. 5,716,616 teaches methods of treating patients who are suffering from a disease, disorder or condition characterized by a bone cartilage or lung defects.

The methods comprising the step of intravenous administration of stromal cells isolated from normal syngeneic individuals or intravenous administration of stromal cells isolated from the patient subsequent to correction of the genetic defect in the isolated cells. Methods of introducing genes into a recipient individual are also disclosed. The methods comprise the steps of obtaining a bone marrow sample from either the recipient individual or a matched syngeneic donor, isolating adherent cells from the sample, transfecting the adherent cells that were isolated from the recipient or a matched syngeneic donor with a gene and administering the transfected adherent cells to the recipient individual intravenously. Compositions that comprise isolated stromal cells that include exogenous genes operably linked to regulatory sequences are disclosed.

In each of the above examples, non-hematopoietic stem and progenitor cells are used as an external source of cells for replenishing missing or damaged cells of an organ. Such use requires cell expansion prior to differentiation in order to first obtain the required cell mass. It is in this step where the method of the present invention can become highly effective and useful while implementing any of the methods disclosed in the above U.S. patents.

Additional examples for both ex-vivo and in-vivo applications: skin regeneration, hepatic regeneration, muscle regeneration and bone growth in osteoporosis.

Mobilization of bone marrow stem cells into the peripheral blood (peripheralization): The discovery of the effect of transition metal chelators could also be applied in-vivo. As mentioned above, PB-derived stem cells for transplantation are "harvested" by repeated leukapheresis following their mobilization from the marrow into the circulation by treatment with chemotherapy and cytokines (3–4).

The use of chemotherapy is, of course, not suitable for normal donors. Administration of transition metal chelators, such as TEPA, into the donor could increase the marrow stem cell pool, which is then mobilized into the periphery by endogenous or injected G-CSF.

Leukemia: Unlike normal hematopoiesis, in leukemia, the processes of proliferation and differentiation are uncoupled; the malignant cells are unable to differentiate and consequently maintain continuous proliferation ability.

Understanding of the molecular events driving the uncoupling of the proliferation and differentiation processes of normal progenitors following transition metals depletion, in particular Copper, may shed light on the cellular processes involved in the development of leukemia.

Stimulation of fetal hemoglobin production: Increased fetal hemoglobin has been shown to ameliorate the clinical symptoms in patients with β-hemoglobinopathies such as sickle cell anemia and β-thalassemia (38).

Fetal hemoglobin, which normally comprises about 1% of the total hemoglobin, becomes elevated in accelerated erythropoiesis (e.g., following acute hemolysis or hemorrhage or administration of erythropoietin) (35).

It has been suggested that this phenomenon is associated with acceleration of the maturation/differentiation process of the erythroid precursors (37).

Administration of transition metal chelators such as TEPA to patients with β-hemoglobinopathies might first increase and synchronize their early erythroid progenitor pool (by blocking differentiation).

Following cessation of administration of the drug and its removal from the body, this early population then might undergo accelerated maturation which may result in elevated production of fetal hemoglobin.

Thus, according to one aspect of the present invention there is provided a method of expanding a population of cells, while at the same time, inhibiting differentiation of the cells. The method includes the step of providing the cells with conditions for cell proliferation and, at the same time, reducing a capacity of the cells in utilizing transition metals, such as Copper.

Reducing the capacity of the cells in utilizing transition metals may be effected, for example, either by depletion thereof (e.g., via suitable chelators) or by interference in their metabolism (e.g., via addition of Zinc ions).

As used herein the term "inhibiting" refers to slowing, decreasing, delaying, preventing or abolishing.

As used herein the term "differentiation" refers to change from relatively generalized to specialized kinds during development. Cell differentiation of various cell lineages is a well documented process and requires no further description herein. As used herein the term differentiation is distinct from maturation which is a process, although some times associated with cell division, in which a specific cell type mature to function and then dies, e.g., via programmed cell death.

According to a preferred embodiment of the present invention the cells to be expanded are present in-vivo. In this case the conditions for cell proliferation are naturally provided. Whereas, reducing the capacity of the cells in utilizing transition metals, such as, but not limited to, Copper is effected by administering a transition metal, e.g., Copper, chelator, Zinc ions, or both.

Administration of the transition metal chelator and/or Zinc ions may be by a pharmaceutical composition including same, which may further include thickeners, carriers, buffers, diluents, surface active agents, preservatives, and the like, all as well known in the art.

The pharmaceutical composition may be administered in either one or more of ways depending on whether local or systemic treatment is of choice, and on the area to be treated. Administration may be done topically (including ophtalmically, vaginally, rectally, intranasally), orally, by inhalation, or parenterally, for example by intravenous drip or intraperitoneal, subcutaneous, intramuscular or intravenous injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons ordinarily skilled in the art can easily determine optimum dosages, dosing methodologies and repetition rates. Slow release administration regime may be advantageous in some applications.

According to another preferred embodiment of the present invention the cells to be expanded are present ex-vivo.

As used herein the term "ex-vivo" refers to cells removed from a living organism and are propagated outside the organism (e.g., in a test tube). As used herein, the term "ex-vivo", however, does not refer to cells known to propagate only in-vitro, such as various cell lines (e.g., HL-60, MEL, HeLa, etc.).

Providing the ex-vivo grown cells with the conditions for cell proliferation include providing the cells with nutrients and preferably with one or more cytokines. Again, reducing the capacity of the cells in utilizing transition metals, such as Copper is effected by a suitable transition metal, e.g., Copper, chelator and/or Zinc ions.

Final concentrations of the chelator and/or Zinc ions may be, depending on the specific application, in the micromolar or millimolar ranges. For example, within about 0.1 $\mu$M to about 100 mM, preferably within about 4 $\mu$M to about 50 mM, more preferably within about 5 $\mu$M to about 40 mM.

According to a preferred embodiment of the invention the chelator is a polyamine chelating agent, such as, but not limited to ethylendiamine, diethylenetriamine, triethylenetetramine, triethylenediamine, tetraethylenepentamine, aminoethylethanolamine, aminoethylpiperazine, pentaethylenehexamine, triethylenetetramine-hydrochloride, tetraethylenepentamine-hydrochloride, pentaethylenehexamine-hydrochloride, tetraethylpentamine, captopril, penicilamine, N,N'-bis(3-aminopropyl)-1,3-propanediamine, N,N,Bis(2 animoethyl) 1,3 propane diamine, 1,7-dioxa-4,10-diazacyclododecane, 1,4,8,11-tetraaza cyclotetradecane-5,7-dione, 1,4,7-triazacyclononane trihydrochloride, 1-oxa-4,7,10-triazacyclododecane, 1,4,8,12-tetraaza cyclopentadecane or 1,4,7,10-tetraaza cyclododecane, preferably tetraethylpentamine. The above listed chelators are known in their high affinity towards Copper ions. However, these chelators have a substantial affinity also towards other transition metals (39). The latter is incorporated by reference as if fully set forth herein.

According to another preferred embodiment of the invention the cytokines are early acting cytokines, such as, but not limited to, stem cell factor, FLT3 ligand, interleukin-6, thrombopoietin and interleukin-3, and/or late acting cytokines, such as, but not limited to, granulocyte colony stimulating factor, granulocyte/macrophage colony stimulating factor and erythropoietin.

The cells may be of any cell lineage including, but not limited to, hematopoietic stem or progenitor cells, neural stem or progenitor cells, oligodendrocyte stem or progenitor cells, skin stem or progenitor cells, hepatic stem or progenitor cells, muscle stem or progenitor cells, bone stem or progenitor cells, mesenchymal stem or progenitor cells, pancreatic stem or progenitor cells, chondrocyte stem or progenitor cells, stroma stem or progenitor cells or embryonal stem cells.

Depending on the application, hematopoictic cells may be obtained for ex-vivo expansion according to the method of the present invention from bone marrow, peripheral blood, or neonatal umbilical cord blood.

Preferably, the hematopoietic cells are enriched for hematopoietic $CD_{34}^+$ cells (i.e., stem cells). Enriching the fraction of stem cells may be effected by cell sorting, as well known in the art.

The cells expanded according to the present invention may be either non-differentiated stem cells or committed progenitor cells. Stem cells are known for many cell lineages, including, but not limited to, those lineages listed hereinabove. These cells are characterized by being the most undifferentiated cells of the lineage. Progenitor cells, on the other hand, are more differentiated, as they are already committed to a specific differentiation path within the cell lineage.

Further according to this aspect of the present invention there is provided a method of hematopoietic cells transplantation. The method includes the following steps. First, hematopoietic cells to be transplanted are obtained from a donor. Second, the cells are provided ex-vivo with conditions for cell proliferation and, at the same time, reducing a capacity of the cells in utilizing transition metals, Copper in particular, thereby expanding a population of the cells, while at the same time, inhibiting differentiation of the cells. Finally, the cells are transplanted to a patient. In a case of an autologous transplantation the donor and the patient are a single individual. The cells may be obtained from peripheral blood, bone marrow or neonatal umbilical cord blood. They are preferably enriched for stem cells or for progenitor cells (e.g., by cell sorting) prior to, or after, cell expansion.

Further according to this aspect of the present invention there is provided a method of genetically modifying (transducing, transfecting, transforming) stem cells with an exogene (transgene). The method includes the following steps. First, stem cells to be genetically modified are obtained. Second, the cells are provided ex-vivo with conditions for cell proliferation and, at the same time, for reducing a capacity of the cells in utilizing transition metals, Copper in particular, thereby expanding a population of the cells, while at the same time, inhibiting differentiation of the cells. Third, the cells are genetically modified with the exogene. Genetic modification methods are well known in the art and require no further description herein. Examples of genetic modification protocols are found in many laboratory manuals including Sambrook, J., Fritsch, E. F., Maniatis, T. (1989) Molecular Cloning. A Laboratory Manual. Cold Spring Harbor Laboratory Press, New York. Genetic modification is preferably effected by a vector including the exogene.

Further according to this aspect of the present invention there is provided a method of adoptive immunotherapy. The method includes the following steps. First, progenitor hematopoietic cells from a patient are obtained. Second, the cells are provided ex-vivo with conditions for cell proliferation and, at the same time, for reducing a capacity of the cells in utilizing transition metals, Copper in particular, thereby expanding a population of the cells, while at the same time, inhibiting differentiation of the cells. Finally, the cells are transplanted into the patient.

Further according to this aspect of the present invention there is provided a method of mobilization of bone marrow stem cells into the peripheral blood of a donor for harvesting the cells. The method includes the following steps. First, the donor is administered with an agent for reducing a capacity of the cells in utilizing transition metals, Copper in particular, thereby expanding a population of stem cells, while at the same time, inhibiting differentiation of the stem cells. Second, the cells are harvested by leukapheresis. Administering the donor a cytokine (early and/or late acting cytokine) is preferred to enhance mobilization. The agent is preferably a transition metal chelator and/or Zinc ions.

Further according to this aspect of the present invention there is provided a method of decelerating maturation/differentiation of erythroid precursor cells for the treatment of β-hemoglobinopathic patients. The method includes the step of administering to the patient an agent for reducing a capacity of the cells in utilizing transition metals, Copper in particular, thereby expanding a population of stem cells, while at the same time, inhibiting differentiation of the stem cells, such that upon natural removal of the agent from the body, the stem cells undergo accelerated maturation resulting in elevated production of fetal hemoglobin.

Further according to this aspect of the present invention there is provided a therapeutical ex-vivo cultured cell preparation. The preparation includes ex-vivo cells propagated in the presence of an agent for reducing a capacity of the cells in utilizing transition metals, Copper in particular, thereby expanding a population of the cells, while at the same time, inhibiting differentiation of the cells.

Further while reducing the present invention to practice it was found that a series of other chemical agents that bind (chelate) Copper and other transition metals and that enhance Copper uptake by cells can reversibly induce or facilitate the process of differentiation of stem cells as well as intermediate and late progenitor cells and thereby impose or accelerate cell differentiation.

This newly discovered effect was utilized for maximizing ex-vivo differentiation of various types of cells.

It was previously shown and it is described hereinabove and exemplified in the Examples section that follows, that a group of Copper-chelating agents, which includes polyamines such as TEPA or chelators such as Penicillamine and Captopril, delays cell differentiation and thereby support continuous cell proliferation and long-term generation of stem and/or progenitor cells of different types. These effects could be overridden by excess of Copper, strongly suggesting that they involve Copper chelation and subsequent Copper prevention.

However now it is disclosed that a second group of transition metal, e.g., Copper chelators, which includes the Copper-binding peptides GGH and GHL (SEQ ID NOS:1 and 2) and the polyamine 1,4,8,11-tetraaza cyclotetradecane, accelerate cell differentiation and thereby limits cell proliferation. The latter effects were also observed, with a similar kinetics, when the cultures were supplemented with late-acting cytokines such as G- and GM-CSF which are known for their ability to accelerate cellular differentiation. Copper salt (1 $\mu$M) had a similar effect.

These results which are presented in the Examples section that follows show that compounds of this group of chelators, i.e., differentiation inducing chelators, as opposed to the former group of chelators, which are differentiation inhibiting chelators, affect the cultures by improving Copper availability to the cellular differentiation mechanism.

It is at present a working hypothesis that the two contrasting effects of Copper-binding compounds are caused by their different Copper binding affinities; differentiation-inhibiting compounds bind Copper with high affinity, substantially irreversibly, and thereby function as chelators that decrease the cellular Copper content, while differentiation-enhancing compounds bind Copper reversibly (with low affinity) and assist in delivering Copper to cellular sites where it is required for differentiation. This hypothesis is not intended to be limiting to the broad scope of the present invention.

The biological properties of the differentiation inducing chelators according to the present invention can be used in several clinical settings, as follows:

Induction of terminal differentiation in acute leukemic cells: The current approach to the treatment of leukemia is based on killing the malignant cells by chemo- or radio-therapy. This treatment is not specific for malignant cells and affects normal cells as well. Indeed, this approach is limited by the toxicity of the treatment to a variety of normal tissues. Since acute leukemia involves a block in cell differentiation, an alternative approach would be to induce the leukemic cells to undergo differentiation which is associated with the loss of leukemogenicity.

Fibach et al. (54) showed that some myeloid leukemia undifferentiated cells respond to differentiation-inducing agents and undergo differentiation into mature, functional, non-dividing granulocytes or macrophages, and thereby, lose their leukemogenic potential. This inducer was identified as Interleukin-6. Although originally purified as a differentiation factor for a mouse myeloid leukemic cell line, it was also found to function as an early hematopoietic growth factor for normal cells.

The differentiation inducing chelators according to this aspect of the present invention were found to induce differentiation and inhibit proliferation of both human and murine established leukemic cell lines and of freshly explanted cells from acute and chronic human myeloid leukemias. Blast cells lose their leukemic phenotype and turn into functional, non-dividing macrophages.

The effect of the differentiation inducing chelators on leukemic cells makes them potentially useful in the treatment of myeloid leukemias in three clinical settings: (a) for induction of remission, either by itself or in combination with other hematopoietic factors or low-dose chemotherapy, using "differentiation-inducing therapy" as the main modality; (b) for maintenance of the remission state; and (c) in autologous transplantation for either ex-vivo or in-vivo purging of residual leukemic cells.

Induction of differentiation of non-leukemic hematopoietic progenitors: Several non leukemic hematological pathological conditions involve a block in cell differentiation. These include "maturation arrest", either idiopathic or drug-induced or in situations like red cell aplasia and congenital neutropenia. The differentiation inducing chelators according to this aspect of the present invention may be useful in these conditions in promoting cell differentiation.

Ex-vivo differentiation of normal stem cells into lineage committed progenitors: For successful transplantation, shortening of the duration of the cytopenic phase, as well as long-term engraftment, is crucial. Inclusion of intermediate and late progenitor cells in the transplant could accelerate the production of donor-derived mature cells and shortens the cytopenic phase. It is important, therefore, that ex-vivo expanded cells will include, in addition to stem cells, more differentiated progenitors, especially those committed to the neutrophilic and megakayocytic lineages, in order to optimize short-term recovery and long term restoration of hematopoiesis. The differentiation inducing chelators according to this aspect of the present invention can serve this purpose.

Ex-vivo differentiation of stem cells into dendritic cell committed progenitors: Dendritic cells are "professional" immunostimulatory, antigen-presenting cells. Various studies have suggested the potential use of dendritic cells in immunotherapy. This modality involves infusion of dendritic cells pulsed in-vivo with tumor antigens as therapeutic vaccines, as well as using dendritic cells for priming tumor antigen specific T cells in-vivo for use in adoptive T cell therapy (55). The differentiation inducing chelators according to this aspect of the present invention may have an effect on the differentiation of these cells.

Thus, according to this aspect of the present invention there is provided a method of in-vivo or ex-vivo induction of differentiation in a population of cells by providing the cells with a transition metal, e.g., Copper, chelator effective in inducing cell differentiation. The method according to this aspect of the present invention can, for example, be used for (i) induction of terminal differentiation in acute leukemic cells; (ii) induction of differentiation of non-leukemic hematopoietic progenitors; (iii) ex-vivo differentiation of normal stem cells into lineage committed progenitors; and/or (iv) ex-vivo differentiation of stem cells into dendritic cell committed progenitors.

According to a preferred embodiment of this aspect of the present invention the cells are hematopoietic cells. Induced differentiation of hematopoietic cells by transition metal chelators is exemplified in the Examples section hereinunder. The cells differentiating by means of a transition metal chelator according to this aspect of the present invention can be normal cells or cancer cells. Thus, cells according to this aspect of the present invention can be derived, for example, from a source such as bone marrow, peripheral blood and neonatal umbilical cord blood. According to an embodiment of this aspect of the present invention the cells are enriched for hematopoietic $CD_{34}^+$ cells. According to another embodiment the cells are non-differentiated stem cells and/or committed progenitor cells. Additionally the cells can be, for example, neural cells and oligodendrocyte cells, skin cells, hepatic cells, muscle cells, bone cells, mesenchymal cells, pancreatic cells, chondrocytes or stroma cells.

Further according to this aspect of the present invention there is provided a pharmaceutical composition for inducing differentiation in a population of cells. The composition according to this aspect of the present invention includes a transition metal chelator of a type and in an amount or concentration effective in inducing cell differentiation and a pharmaceutically acceptable carrier.

According to an embodiment of this aspect of the present invention the transition metal chelator is a tripeptide, e.g., GGH and/or GHL. Both are shown in the Examples section hereinunder to induce differentiation. Thus, the transition metal chelator according to this aspect of the present invention is a peptide or a peptide analog, or it includes a peptide sequence.

As used herein in the specification and in the claims section below the term "peptide" refers to native peptides (either degradation products or synthetically synthesized peptides) and further to peptidomimetics (peptide analogs), such as peptoids and semipeptoids, which may have, for example, modifications rendering the peptides more stable while in a body, or more effective in chelating under physiological conditions. Such modifications include, but are not limited to, cyclization, N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified in Quantitative Drug Design, C. A. Ramsden Gd., Chapter 17.2, F. Choplin Pergamon Press (1992), which is incorporated by reference as if fully set forth herein.

As used herein the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Administration of the differentiation inducing transition metal chelator can be effected by a pharmaceutical composition including same, which may further include a pharmaceutically acceptable carriers, such as thickeners, buffers, diluents, surface active agents, preservatives, and the like, all as well known in the art and as is further described above with respect to differentiation inhibiting chelators.

Thus, while conceiving and reducing to practice the present invention it was found that transition metal chelators which bind copper are either differentiation inducers or inhibitors. It is believed that differentiation inhibiting chelators are either binding Copper so efficiently, or cannot enter the cell of present the cell with copper, so as to reduce Copper availability to the cell and eventually reduce Copper content in the cell, a result of which is differentiation arrest and cell expansion, which can be reversed by Copper addition to the growth medium of the expanding cells. It is further believed that differentiation inducing chelators are either binding Copper less efficiently, and can enter the cell of present the cell with copper, so as to increase Copper availability to the cell and eventually increase Copper content in the cell, a result of which is differentiation acceleration and inhibited proliferation. These assumptions gain strength by the fact that while chelators inducing differentiation bring about substantial increase in cellular Copper levels, whereas while chelators inhibiting differentiation bring about decrease in cellular Copper levels.

Based on these findings the present invention offers two independent or supplementary tests for identifying differentiation inducing and inhibiting chelators.

Thus, according to another aspect of the present there is provided an assay of determining whether a transition metal chelator which binds copper causes inhibition or induction of differentiation. The assay according to this aspect of the invention is effected by culturing a population of stem or progenitor cells or cells of a substantially non-differentiated cell line, in the presence of the transition metal chelator and monitoring differentiation of the cells, wherein if differentiation is increased as is compared to non-treated cells, the transition metal chelator induces differentiation, whereas if differentiation is decreased as compared to non-treated cells, or if differentiation is absent altogether, the transition metal chelator inhibits differentiation.

According to another aspect of the present there is provided an assay of determining whether a transition metal chelator which binds copper causes inhibition or induction of differentiation. The assay according to this aspect of the invention is effected by culturing a population of cells in the presence of the transition metal chelator and monitoring copper content of the cells, wherein if the copper content of the cells is increased as is compared to non-treated cells, the transition metal chelator induces differentiation, whereas if the copper content is decreased as compared to non-treated cells the transition metal chelator inhibits differentiation.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Cell Biology: A Laboratory Handbook" Volumes I–III Cellis, J. E., ed. (1994); "Current Protocols in Immunology" Volumes I–III Coligan J. E., ed. (1994); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods and Enzymology" Vol. 1–317 Academic Press; all of which are incorporated by reference as if fully set forth herein. Other general references are provided throughout this document. The procedures therein are believed to be well known in the art and are provided for the convenience of the reader. All the information contained therein is incorporated herein by reference.

Example 1

Imposing Proliferation Yet Restricting Differentiation of Stem and Progenitor Cells by Treating the Cells with Chelators of Transitional Metals Experimental Procedures $CD_{34}$ cells selection: Peripheral blood "buffy coat" cells derived from a whole blood unit, peripheral blood cells obtained following leukapheresis, or cord blood cells were layered on Ficoll-Hypaque (density 1.077 g/ml) and centrifuged at 1,000×g for 20 min. at room temperature. The interphase layer of mononuclear cells were collected, washed three times with Ca/Mg free phosphate buffered saline containing 1% bovine serum albumin (BSA). The cells were incubated for 30 min. at 4° C. with murine monoclonal anti $CD_{34}$ antibody (0.5 µg/$10^6$ mononuclear cells) and thereafter isolated using the miniMACS apparatus (Miltenyi-Biotec, Bergisch, Gladbach, Germany) according to the manufacturer's protocol.

Culture procedures: For the expansion of progenitor cells, $CD_{34}^+$ enriched fractions or unseparated mononuclear cells were seeded at about 1–3×$10^4$ cells/ml in either alpha minimal essential medium containing 10% preselected fetal calf serum (FCS) (both from GIBCO, Grand Island, N.Y.), or serum-free medium (Progenitor-34 medium, Life Technologies, Grand Island, N.Y.). The media were supplemented with a mixture of growth factors and transition metal chelators. The cultures were incubated at 37° C. in an atmosphere of 5% $CO_2$ in air with extra humidity. Half of the medium was changed weekly with fresh medium containing all the supplements.

Cloning potential evaluations: The cloning potential of cells developed in the liquid culture was assayed, at different intervals, in semi-solid medium. The cells were washed and seeded in 35 mm dishes in methylcellulose containing alpha medium supplemented with recombinant growth factors (SCF, G-CSF, GM-CSF and EPO). Following 2 weeks incubation, the cultures were scored with an inverted microscope. Colonies were classified as blast, mixed, erythroid, myeloid, and megakaryocytic, according to their cellular composition.

Morphological assessment: In order to characterize the resulting culture populations, aliquots of cells were deposited on a glass slide (cytocentrifuge, Shandon, Runcorn, UK), fixed and stained in May-Grunwald Giemsa. Other aliquots were stained by benzidine for intracellular hemoglobin.

Immunofluorescence staining: At different intervals, cells from the liquid cultures were assayed for $CD_{34}$ antigen. Aliquots were harvested, washed and incubated on ice with FITC-labeled anti $CD_{45}$ monoclonal antibody and either PE-labeled anti $CD_{34}$ (HPCA-2) monoclonal antibody or PE-labeled control mouse Ig. After incubation, red cells were lysed with lysing solution, while the remaining cells were washed and analyzed by flow cytometer.

Flow cytometry: Cells were analyzed and sorted using FACStarPlus flow cytometer (Becton-Dickinson, Immunofluorometry systems, Mountain View, Calif.). Cells were passed at a rate of 1,000 cells/second through a 70 mm nozzle, using saline as the sheath fluid. A 488 nm argon laser beam at 250 mW served as the light source for excitation. Green (FITC-derived) fluorescence was measured using a 530±30 nm band-pass filter and red (PE-derived) fluorescence—using a 575±26 nm band filter. The PMTs was set at the appropriate voltage. Logarithmic amplification was applied for measurements of fluorescence and linear amplification—for forward light scatter. At least $10^4$ cells were analyzed.

Experimental Results

In an effort to develop culture conditions which stimulate proliferation and inhibit differentiation of hematopoietic progenitor cells, $CD_{34}^+$ cells were cultured with the following supplements:

Transition metal chelators such as—tetraethylpentamine (TEPA), captopril (CAP) penicilamine (PEN) or other chelators or ions such as Zinc which interfere with transition metal metabolism;

Early-acting cytokines—stem cell factor (SCF), FLT3 ligand (FL), interleukin-6 (IL-6), thrombopoietin (TPO) and interleukin-3 (IL-3);

Late-acting cytokines—granulocyte colony stimulating factor (G-CSF), granulocyte/macrophage colony stimulating factor (GM-CSF) and erythropoietin (EPO).

TEPA effects on proliferation and clonability of short term $CD_{34}+$ cultures: Addition of TEPA to $CD_{34}^+$ cells cultured with low doses of early-acting cytokines resulted in a significant increase in total cell number, in the number of $CD_{34}^+$ cells (measured by flow cytometry utilizing fluorescence labeled specific antibodies, FIG. 2) and in cell clonability (measured by plating culture aliquots in semi-solid medium and scoring colonies that develop two weeks later, FIG. 1), compared to cultures supplemented only with cytokines. The colonies which developed in semi-solid medium in the presence of TEPA were of myeloid, erythroid and mixed phenotype.

Figure 2:
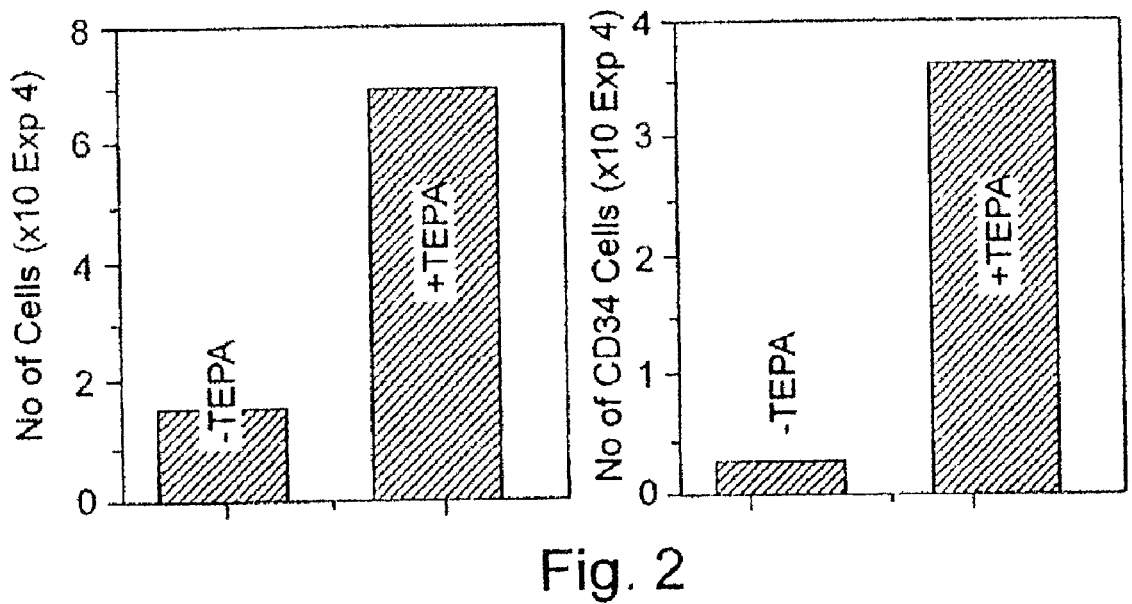
FIG. 2 shows the short-term effect of TEPA on total and $CD_{34}$ cells. Cord blood-derived $CD_{34}$ cells were plated in liquid culture in the presence of FL—5 ng/ml, SCF—10 ng/ml, IL-6—10 ng/ml, with or without of TEPA (20 $\mu$M). On day 7, the wells were demi-depopulated by removal of one half the culture volume and replacing it with fresh medium and IL-3 (20 ng/ml). On day 14, the percentage of $CD_{34}$ cells (right) and the total cell number (left) multiplied by the dilution factor were determined.
Figure 3A:
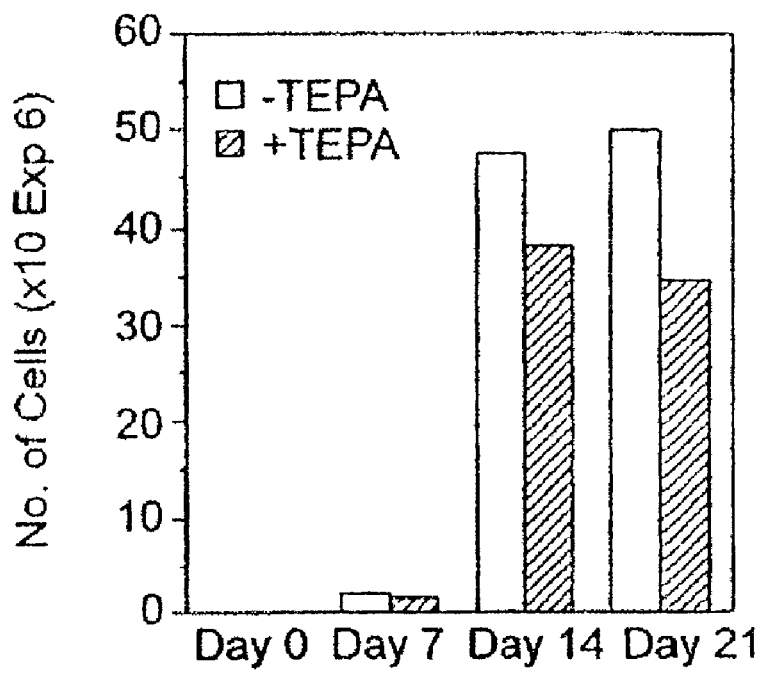
FIG. 3 shows the long-term effect of TEPA on cell number and clonogenic potential of $CD_{34}$ cells. Cord blood-derived $CD_{34}$ cells were plated in liquid culture, at $3 \times 10^4$ cells/ml, in the presence of high dose cytokines: FL—50 ng/ml, SCF—50 ng/ml, IL-6—50 ng/ml, IL-3—20 ng/ml, G-CSF—10 ng/ml, EPO—1 U/ml, with or without TEPA (20 $\mu$M). On day 4, the cultures were diluted 1:10 with 0.9 ml fresh medium supplemented with cytokines and TEPA. On day 7, 14 and 21, the cultures were demi-depopulated by removal of one half the culture volume and replacing it with fresh medium, cytokines and TEPA, as indicated. Cells of the harvested medium were count and aliquots equivalent to $1 \times 10^3$ initiating cells were cloned in semi-solid medium. The numbers of cells (up) in the liquid culture and of colonies (down) in the semi-solid culture, multiplied by the dilution factors, are represented. * denotes small colonies and cell clusters.
Figure 3B:
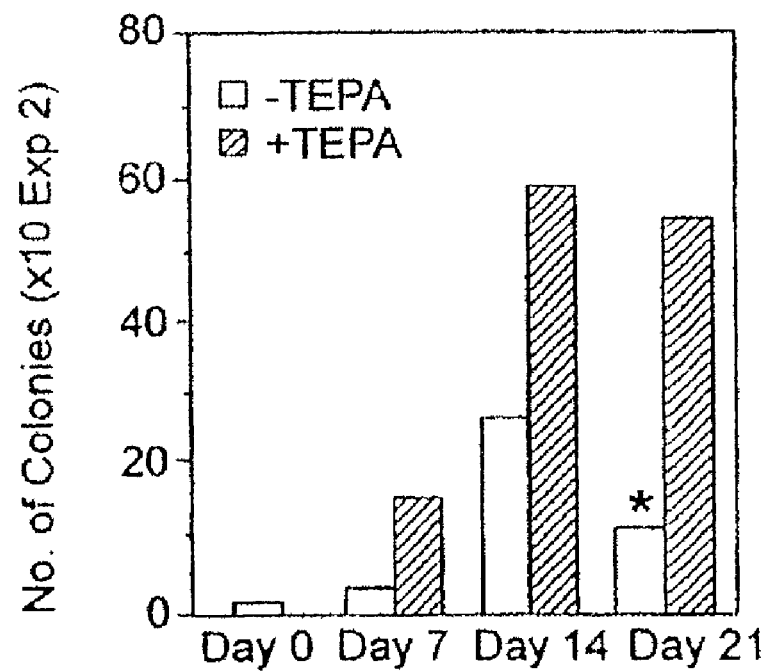

The effects of TEPA were further assessed in cultures supplemented with either high doses of early cytokines (Table 1) or with a combination of early- and late-acting cytokines (FIG. 3). The results indicated that TEPA significantly increased the clonability and the percentage of $CD_{34}^+$ cells in these cultures. As for total cell number it was increased by TEPA in cultures supplemented with early cytokines (Table 1; FIG. 2), whereas in cultures supplemented with both early and late cytokines, TEPA caused a marginal inhibition (FIG. 3).

Cord blood-derived $CD_{34}$ cells were plated in liquid culture in the presence of: FL—50 ng/ml, SCF—50 ng/ml, IL-6—50 ng/ml, with or without IL-3—20 ng/ml, with or without TEPA—10 µM. On day 7, the percentage of $CD_{34}$ cells and the total cell number were determined. Aliquots equivalent to 1×$10^3$ initiating cells were assayed on days 0 and 7 for colony forming cells (CFU) by cloning in semi-solid medium. CFU expansion represents the ratio of CFU present on day 7 to CFU present on day 0.

TABLE 1

The short-term effect of TEPA on $CD_{34}$ cells

| TEPA | Il-3 | Cells/ml (×10$^4$) | $CD_{34}$ cells (%) | Colonies (Per 1 × 10$^3$ initiating cells) | CFU expansion (fold) |
|---|---|---|---|---|---|
| − | − | 1 | 1 | 16 | 0.3 |
| + | − | 2 | 11.5 | 140 | 2.8 |
| − | + | 5 | 5 | 165 | 3.3 |
| + | + | 11 | 20 | 850 | 17 |

Figure 4A:
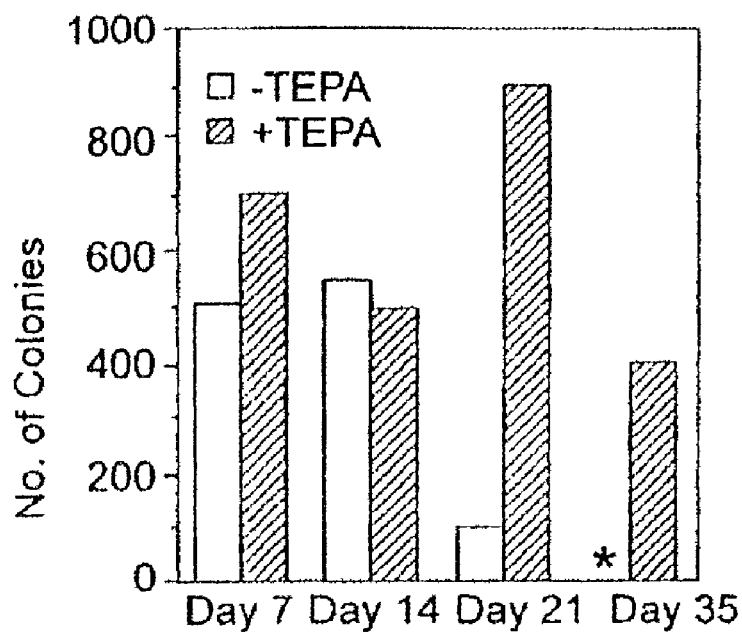
FIG. 4 shows the long-term effect of TEPA on $CD_{34}$ cells cultured with early cytokines. Cord blood-derived $CD_{34}$ cells were plated in liquid culture in the presence of: FL—50 ng/ml, SCF—50 ng/ml and thrombopoietin (TPO)—20 ng/ml, with or without TEPA (10 $\mu$M). At weekly intervals, the cultures were demi-depopulated by removal of one half the culture volume and replacing it with fresh medium, cytokines and TEPA, as indicated. Cells of the harvested medium were count and aliquots equivalent to $1 \times 10^3$ initiating cells were cloned in semi-solid medium. The numbers of cells (down) in the liquid culture and of colonies (up) in the semi-solid culture, multiplied by the dilution factors, are represented. * denotes that no colonies developed.
Figure 4B:
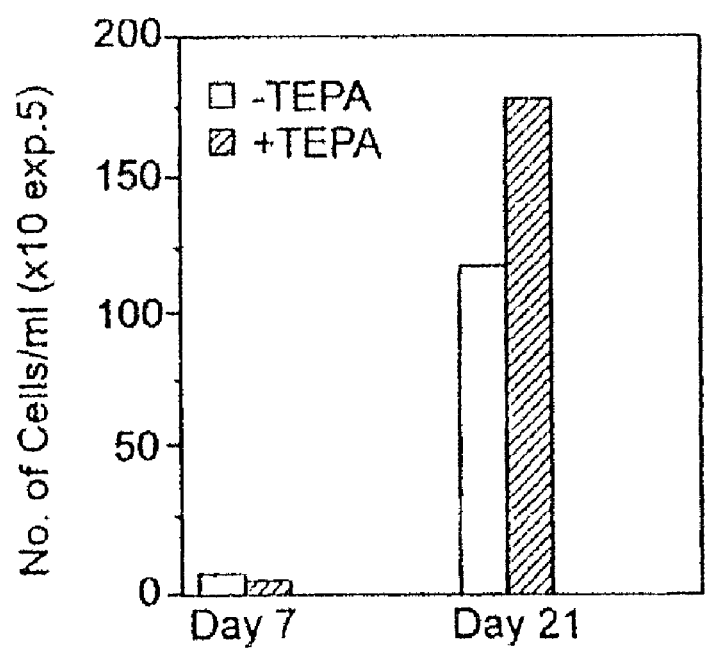

TEPA effects on proliferation and clonability of long-term $CD_{34}^+$ cultures: Long-term cultures were maintained for 3–5 weeks by weekly demi-depopulation (one half of the culture volume was removed and replaced by fresh medium and cytokines). Addition of TEPA resulted in a higher clonability in long-term cultures supplemented with either early cytokines (FIG. 4) or both early and late cytokines (FIG. 3), as compared to cultures supplemented only with cytokines.

After three weeks in culture, there was a sharp decrease in clonability in cultures supplemented only with cytokines, whereas cultures treated with TEPA in combination with cytokines maintained high clonability, which was even higher than that of short-term cultures.

The effect of TEPA on the maturation of hematopoietic cells: The effect of TEPA on the maturation of hematopoietic cells was tested on several models:

Mouse erythroleukemic cells (MEL): MEL cells are erythroblast like cells. Following treatment with several chemicals (differentiation inducers) the cells undergo erythroid differentiation and accumulate hemoglobin. MEL cells were cultured in the presence of the differentiation inducer hexamethylene bisacetamide (HMBA) and the chelators TEPA or Captopril. At day 3 of the culture, the total number of cells and the percentage of hemoglobin-containing cells were determined (Table 2). The results indicated that both TEPA and captopril inhibited the HMBA-induced differentiation of MEL cells.

Human erythroid cell cultures: Normal human eryhroid cells were grown according to the two-phase liquid culture procedure, essentially as described in references 23–26. In the first phase, peripheral blood mononuclear cells were incubated in the presence of early growth factors for 5–7 days. In the second phase, these factors were replaced by the erythroid specific proliferation/differentiation factor, erythropoietin.

Figure 5:
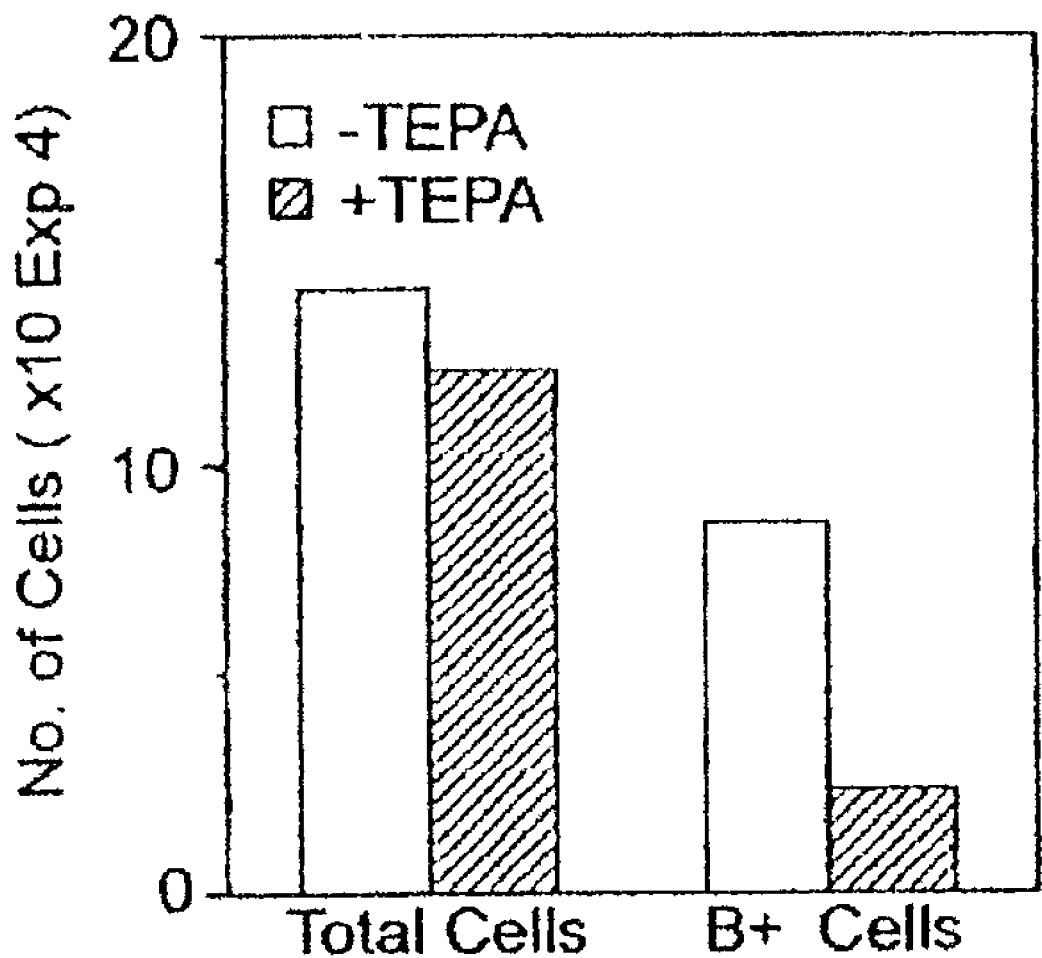
FIG. 5 shows the effect of TEPA on development of erythroid precursors. Peripheral blood mononuclear cells, obtained from an adult normal donor, were cultured in the erythroid two-phase liquid culture system (23–25). The second phase of the culture was supplemented either without or with 10 μM of TEPA. Cultures were analyze for total cells and hemoglobin-containing [benzidine positive (B+)] cells after 14 days.
Figure 6A:
FIGS. 6a–d show the effect of TEPA on cell maturation. Morphology of cells in long-term (7 weeks) cultures in the absence (6a and 6c) and presence (6b and 6d) of TEPA is shown. Cytospin prepared slides were stained with May-Grunwald Giemsa. Magnifications: 6a and 6b×600; 6c and 6d×1485.
Figure 6B:
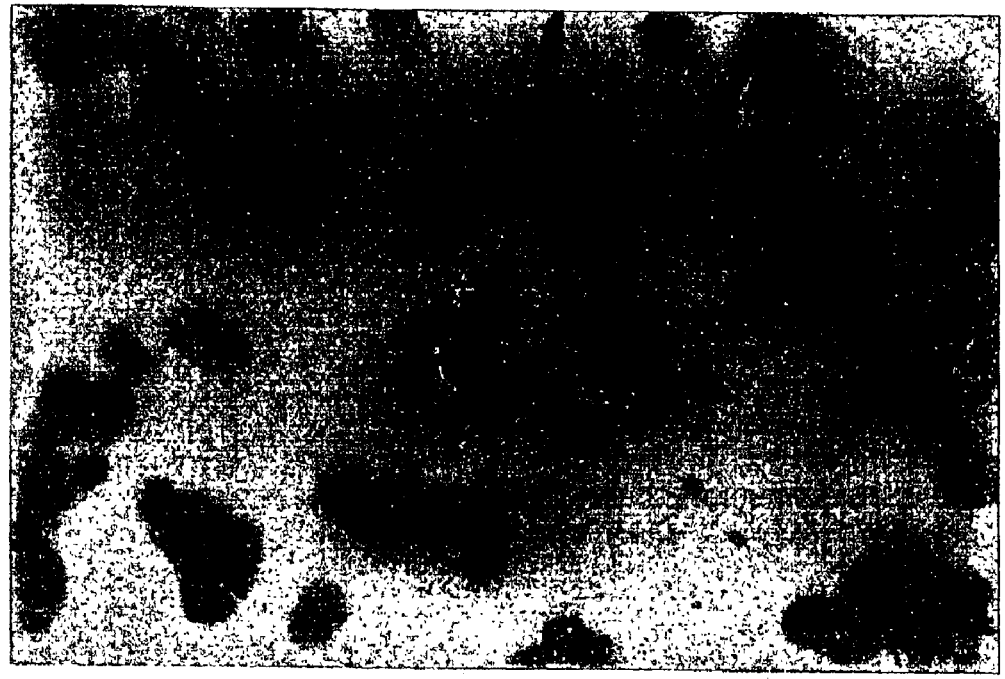
Figure 6C:
Figure 6D:
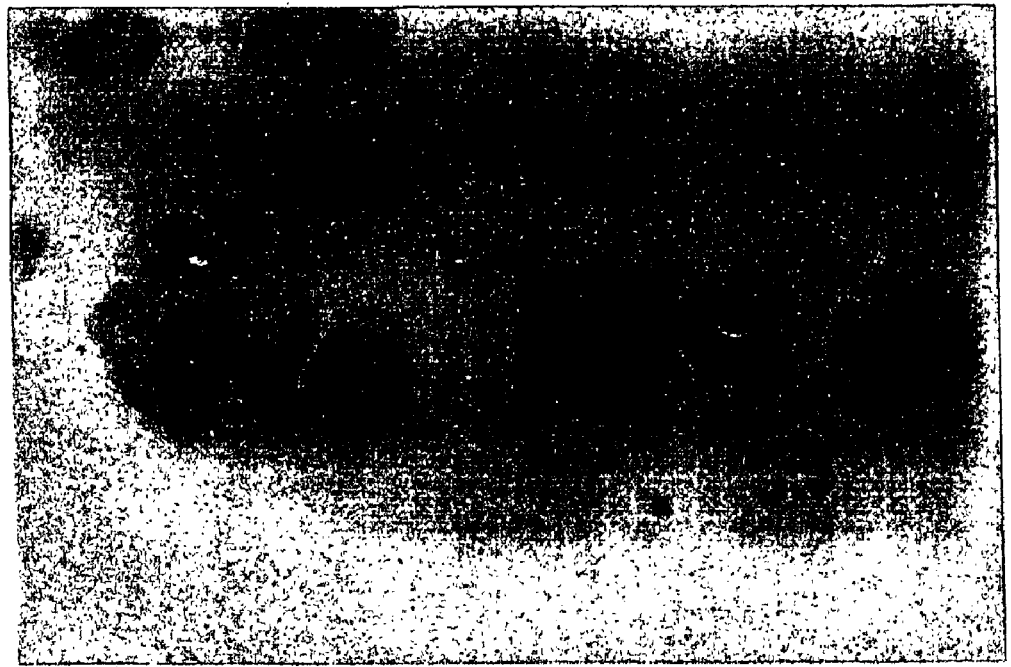

The cultures were supplemented with TEPA at the initiation of the second phase. The total cell number and the percentage of hemoglobin-containing cells were determined after 14 days. The results (FIG. 5) showed that in the presence of TEPA there was a sharp decrease in hemoglobin-containing cells, while the total number of cells decreased only slightly.

These results suggest that TEPA inhibits erythroid differentiation, but does not significantly affect the proliferation ability of the progenitor cells.

TABLE 2

The effect of TEPA and captopril on growth and differentiation of erythroleukemic cells

|  | Cells/ml (×10$^4$) | Benzidine Positive Cells (%) |
|---|---|---|
| Control | 31 | <1 |
| HMBA | 32 | 46 |
| HMBA + TEPA 5 μM | 35 | 24 |
| HMBA + TEPA 10 μM | 35 | 16 |
| HMBA + TEPA 20 μM | 47 | 16 |
| HMBA + Captopril 20 μM | 34 | 29 |
| HMBA + Captopril 40 μM | 34 | 12 |

Murine erythroleukemia cells (MEL), were cultured in liquid medium supplemented with the differentiation inducer—hexamethylene-bisacetamide (HMBA, 4 mM), with or without different concentrations of TEPA or captopril. On day 3, total cell number and hemoglobin containing (benzidine positive) cells were determined.

$CD_{34}^+$ initiated cultures: Long term liquid cultures initiated with $CD_{34}^+$ cells were maintain with different cocktails of cytokines. Half of the cultures were continuously supplemented with TEPA. In order to test the status of cell differentiation, cytospin preparation were stained with May-Grunwald Giemsa (FIGS. 6a–d). The results showed that cultures which were maintained for 4–5 weeks without TEPA contained only fully differentiated cells, while with TEPA the cultures contained, in addition to fully differentiated cells, a subset of 10%–40% of undifferentiated blast-like cells.

These results strongly suggest that TEPA induces a delay in $CD_{34}^+$ cell differentiation which results in prolonged proliferation and accumulation of early progenitor cells in long-term ex-vivo cultures.

TEPA's mechanism of activity: In order to determine whether TEPA affects $CD_{34}^+$ cells via depletion of transition metals, such as Copper, two approaches were taken.

Figure 7:
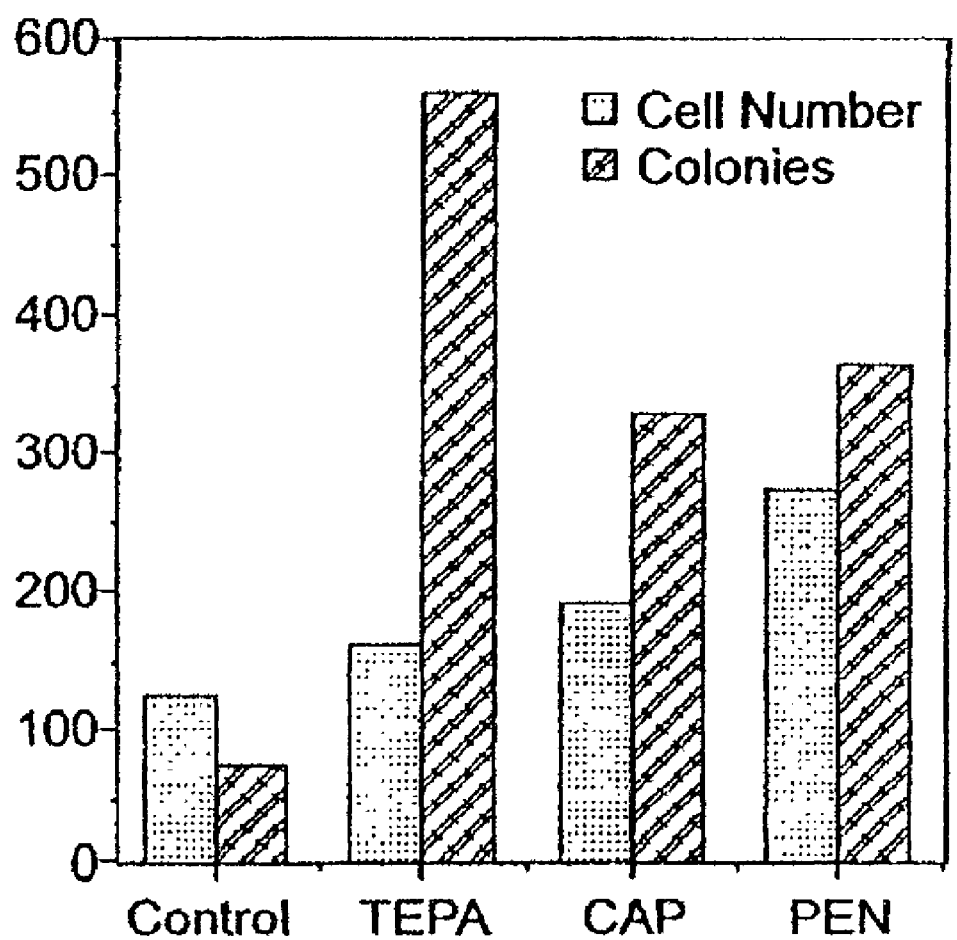
FIG. 7 shows the effect of transition metal chelators on cell number and clonogenic of $CD_{34}$ cells initiated cultures. Cord blood-derived $CD_{34}$ cells were plated in liquid cultures in the presence of FL—20 ng/ml, SCF—20 ng/ml, IL-3—20 ng/ml, IL-6—20 ng/ml, and either TEPA—10 μM, captopril (CAP)—10 μM or Penicillamine (PEN)—10 μM, as indicated. On day 7, cells were counted and culture aliquots equivalent to 1×10³ initiating cells were plated in semi-solid medium. The bars present the total cell number (×10 ³/ml) on day 7 and the number of colonies per plate 14 days following cloning.

The first was to assess the effect of different transition metal chelators: tetra-ethylpentamine (TEPA), captopril (CAP) or penicilamine (PEN). The results demonstrated that all these compounds share the same effects on $CD_{34}^+$ cells as TEPA (FIG. 7).

Figure 8A:
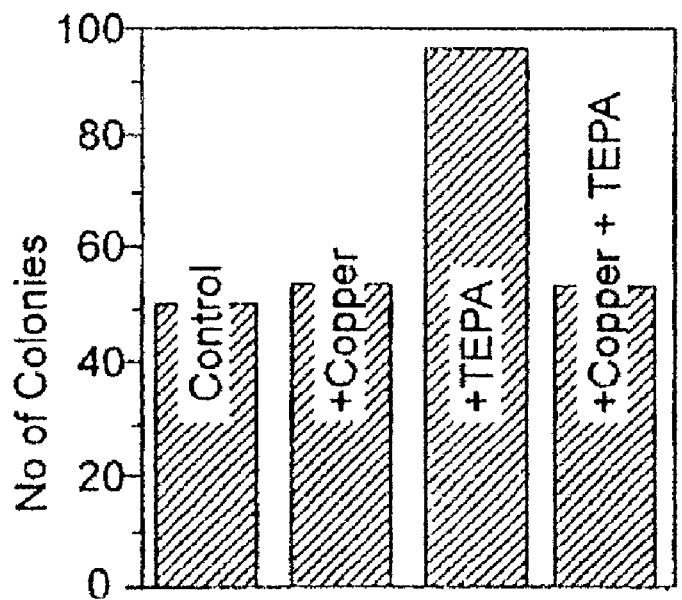
FIG. 8 shows the effect of Copper on the clonogenic potential and total cell number of $CD_{34}$ cells. Cord blood-derived $CD_{34}$ cells were plated in liquid cultures in the presence of cytokines: FL—10 ng/ml, SCF—10 ng/ml, IL-3—10 ng/ml, IL-6—10 ng/ml. Cultures were supplemented with Copper-sulfate—5 μM and TEPA—20 μM, as indicated. On day 7, cells were counted (down) and aliquots equivalent to 1×10³ initiating cells were plated in semi-solid medium. Colonies were scored after 14 days (up).
Figure 8B:
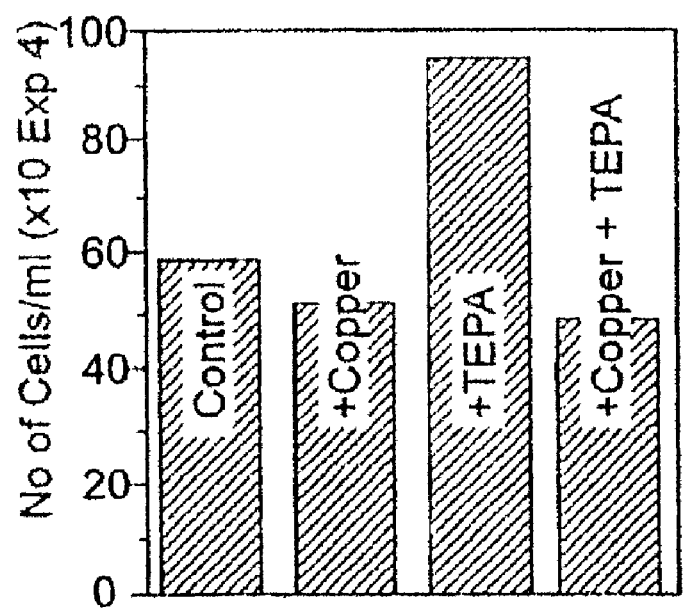
Figure 9:
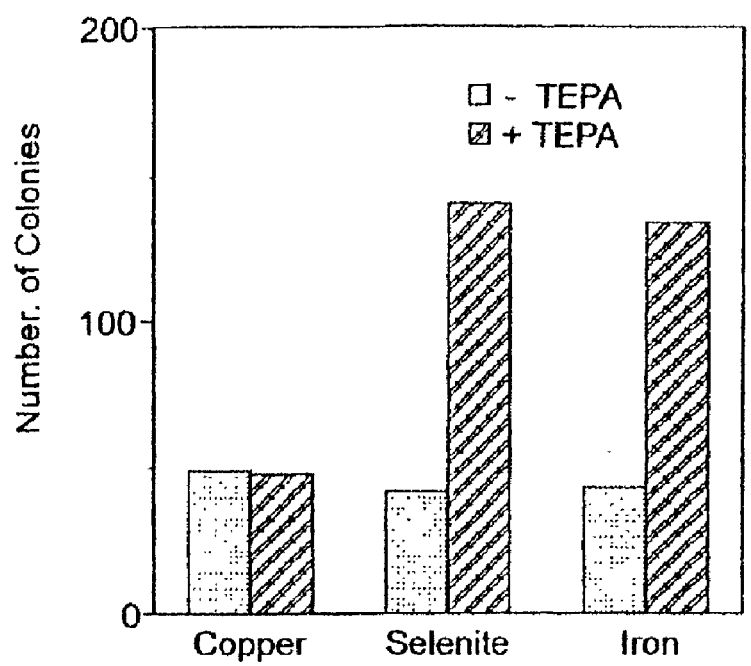
FIG. 9 shows the effect of ions on the clonogenic potential of cultured $CD_{34}$ cells. Cord blood-derived $CD_{34}$ cells were plated in liquid cultures in the presence of FL—10 ng/ml, SCF—10 ng/ml, IL-3—10 ng/ml, IL-6—10 ng/ml, and either with or without TEPA—10 μM. The cultures were supplemented with Copper-sulfate—5 mM, sodium selenite—5 mM or iron-saturated transferrin 0.3 mg/ml, as indicated. On day 7, culture aliquots equivalent to 1×10³ initiating cells were plated in semi-solid medium. Colonies were scored after 14 days.

The second approach was to supplement TEPA-treated cultures with Copper. The results indicated that TEPA activities were reversed by Copper (FIG. 8), while supplementation with other ions, such as iron and selenium, did not (FIG. 9), at least in the short to medium term cultures employed herein.

Figure 10:
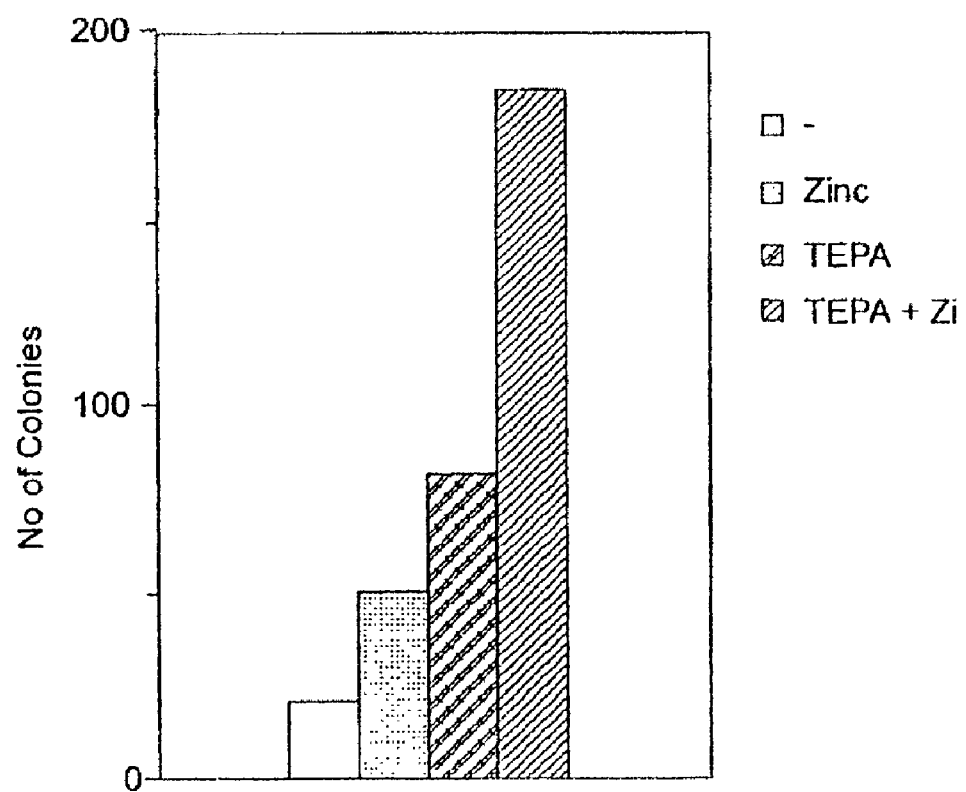
FIG. 10 shows the effect of Zinc on the proliferative potential of $CD_{34}$ cells. Cord blood-derived $CD_{34}$ cells were plated in liquid cultures in the presence of FL—10 ng/ml, SCF—10 ng/ml, IL-3—10 ng/ml, IL-6—10 ng/ml, and either TEPA—10 μM or Zinc-sulfate—5 mM or both. On day 7, aliquots equivalent to 1×10³ initiating cells were plated in semi-solid medium. Colonies were scored after 14 days.

Zinc, which is known to interfere with transition metal metabolism, e.g., with Copper metabolism, expand the clonability of the cultures by itself. This effect was even more pronounced in the presence of both Zinc and TEPA (FIG. 10).

In the above examples it is demonstrated that by supplementing $CD_{34}$ cell cultures with early-acting cytokines and the polyamine agent—tetraethylenepentamine (TEPA), for example, it is possible to maintain long term cultures (LTC) without the support of stroma. Three phenomena were evident in these cultures: (i) continues cell proliferation; (ii) expansion of clonogenic cells (CFUc); and (iii) maintenance of cells at their undifferentiated status.

In contrast, control, TEPA-untreated cultures ceased to proliferate and to generate CFUc and their cells underwent differentiation much earlier.

Thus, TEPA and other transition metal chelators sustains long-term cultures by inhibiting/delaying cellular differentiation through chelation of transition metals, Copper in particular.

The following example further substantiate the results described hereinabove; teaches optimal culture conditions for long-term cultures, teaches additional chelating agents that affect hematopoietic cell differentiation and sheds more light on the mechanism of activity of TEPA and other chelators on their target cells.

$CD_{34}^+$ cells derived from human neonatal cord blood were purified by immunomagnetic method and then cultured in liquid medium supplemented with cytokines either with or without transition metal chelators. At weekly intervals, the cultures were demi-depopulated by removing half of the culture content (supernatant and cells) and replacing it with fresh medium, cytokines and the chelators. At the indicated weeks the cellular content of the cultures were quantified for total cells (by a manual microscopic/hemocytometric method), for $CD_{34}^+$ cells (by immuno-flow cytometry) and for clonogenic cells (by cloning the cells in cytokine-supplemented semi-solid medium). The cultures were initiated with $1\times10^4$ cells, 50–80% of which were $CD_{34}^+$ and 25–50% of which were CFUc. The results presented in FIGS. 11 to 24 were calculated per $1\times10^4$ initiating cells (the numbers were multiplied by the dilution factors).

Figure 11A:
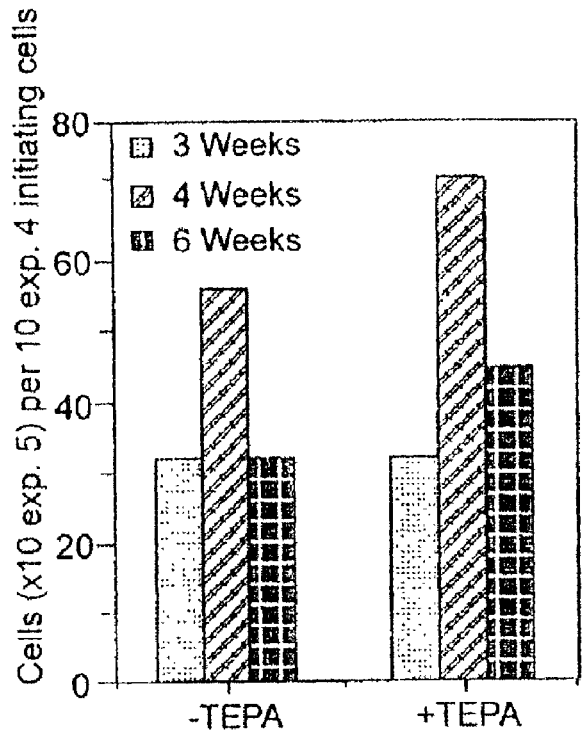
FIGS. 11a–c show the effect of TEPA on long-term $CD_{34}$ cultures. Cultures were initiated with 10⁴ cord blood-derived $CD_{34}$ cells by plating purified cells in liquid medium in the presence of SCF, FLT3 and IL-6 (50 ng/ml each) and IL-3 (20 ng/ml) with or without TEPA (10 μM). At weekly intervals, the cultures were demi-depopulated by removal of half the cells followed by addition of fresh medium, cytokines and TEPA. At the indicated weeks, cells were counted and assayed for colony forming cells (CFUc) by cloning in semi-solid medium. CFUc frequency was calculated as number of CFUc per number of cells. Cloning of purified $CD_{34}$ cells on day 1 yielded 2.5×10³ CFUc per 10⁴ initiating cells. * denotes that no colonies developed.
Figure 11B:
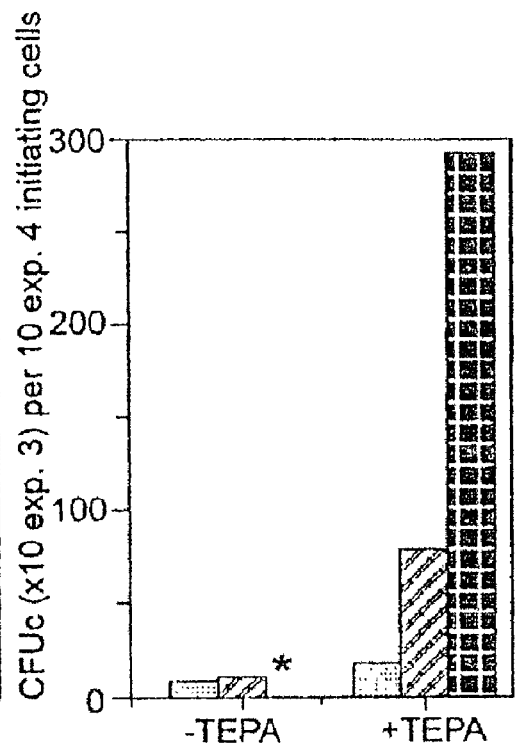
Figure 11C:
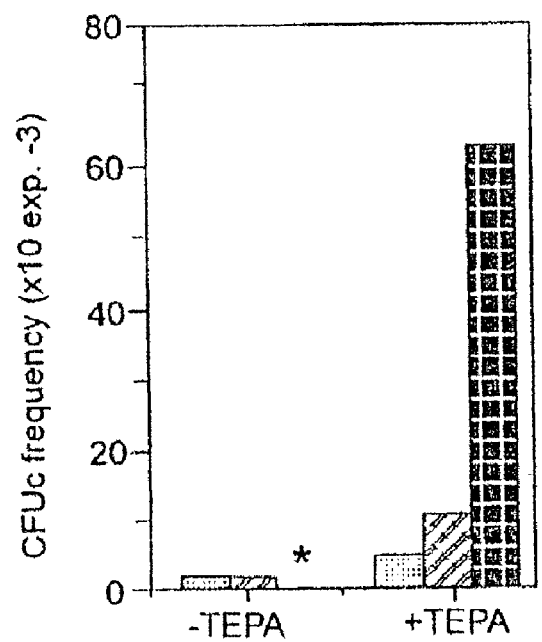

FIG. 11 shows the effect of TEPA on long-term $CD_{34}$ cultures. Cultures initiated with $CD_{34}$ cells in liquid medium supplemented with early-acting cytokines (in the absence of stromal cells) could be maintained by TEPA for a long time (>6 weeks). In such cultures, TEPA supported, in combination with the cytokines, maintenance and expansion of clonogenic cells (CFUc): The cultures were started with $2.5\times10^3$ CFUc. Upon termination after 6 weeks, TEPA-treated cultures contained $300\times10^3$ CFUc, (i.e., a 120-fold expansion) while control cultures contained no CFUc.

Figure 12:
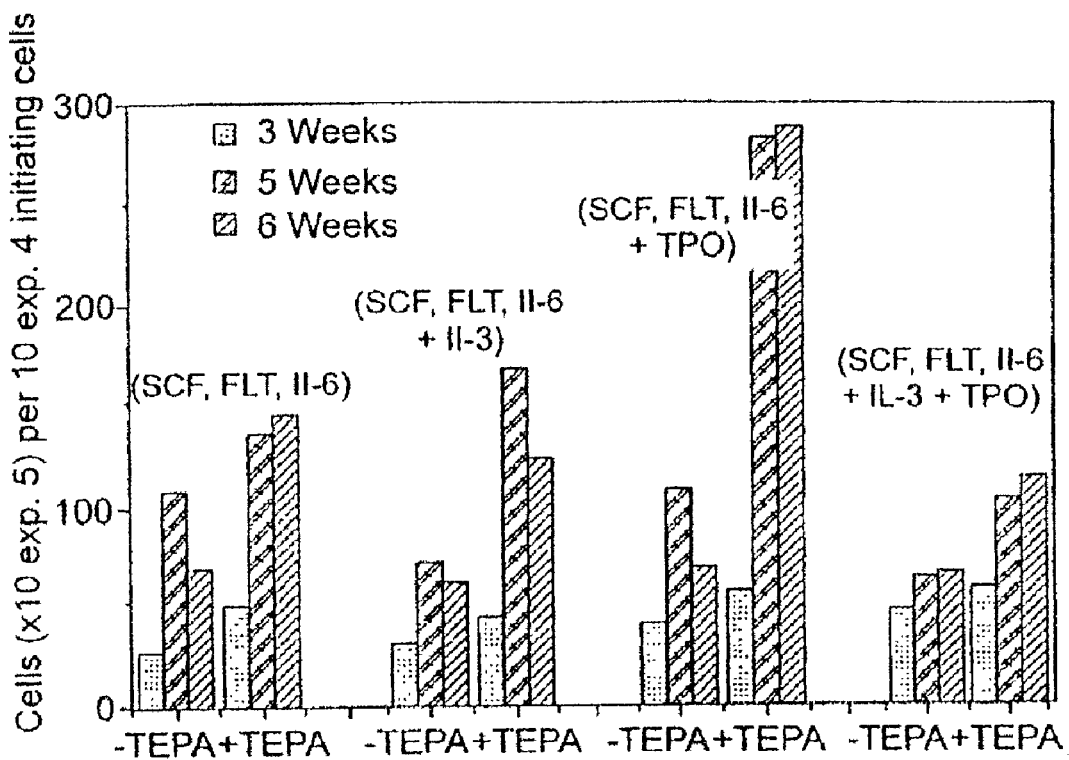
FIGS. 12–14 show the effect of TEPA on cell proliferation, CFUc and CFUc frequency in the presence of different combination of early cytokines. Cord blood-derived $CD_{34}$ cells were cultured as detailed in FIGS. 11a–c in liquid medium in the presence of SCF, FLT3 and IL-6 (SCF, FLT, Il-6), each at 50 ng/ml, with or without TEPA (10 μM). In addition, cultures were supplemented with either IL-3 (20 ng/ml), TPO (50 ng/ml) or both, as indicated. At weekly intervals, the cultures were demi-depopulated and supplemented with fresh medium, cytokines and TEPA. At the indicated weeks, the cells were counted (FIG. 12), assayed for CFUc (FIG. 13) and the CFUc frequency calculated (FIG. 4). * denotes that no colonies developed.
Figure 13:
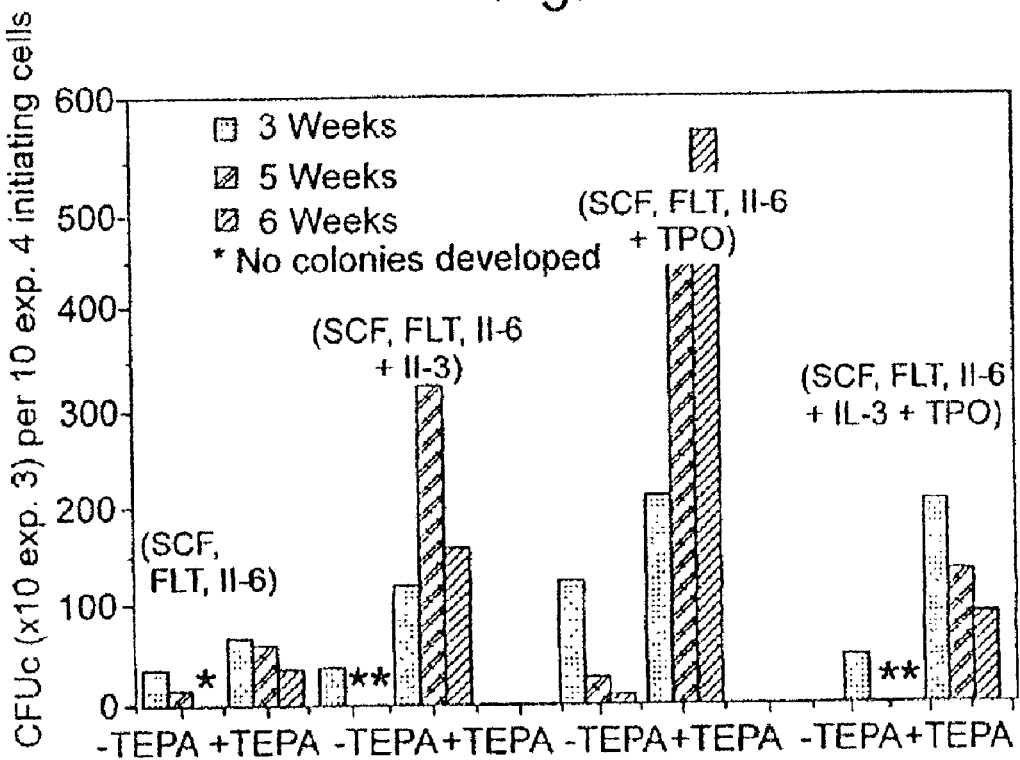
Figure 14:
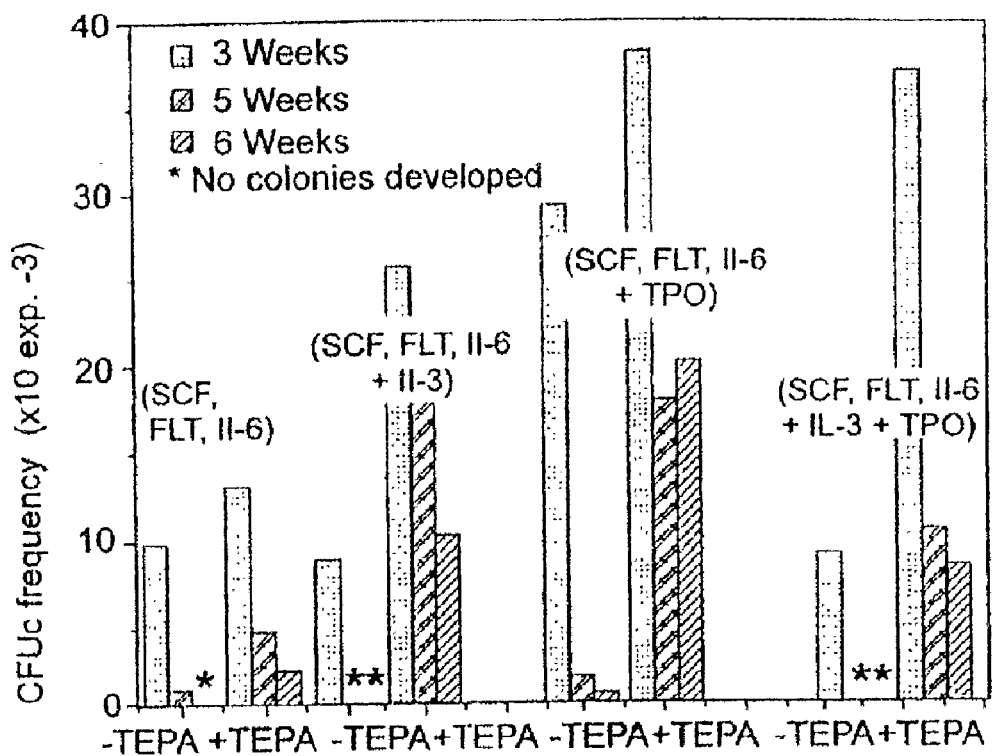

FIGS. 12–14 show the effect of TEPA on cell proliferation, CFUc and CFUc frequency in the presence of different combination of early cytokines. The combination of the early-acting cytokines TPO, SCF, FLT, IL-6 and TEPA was found to be the optimal combination for the maintenance and long term expansion of cells with clonogenic potential.

Figure 15:
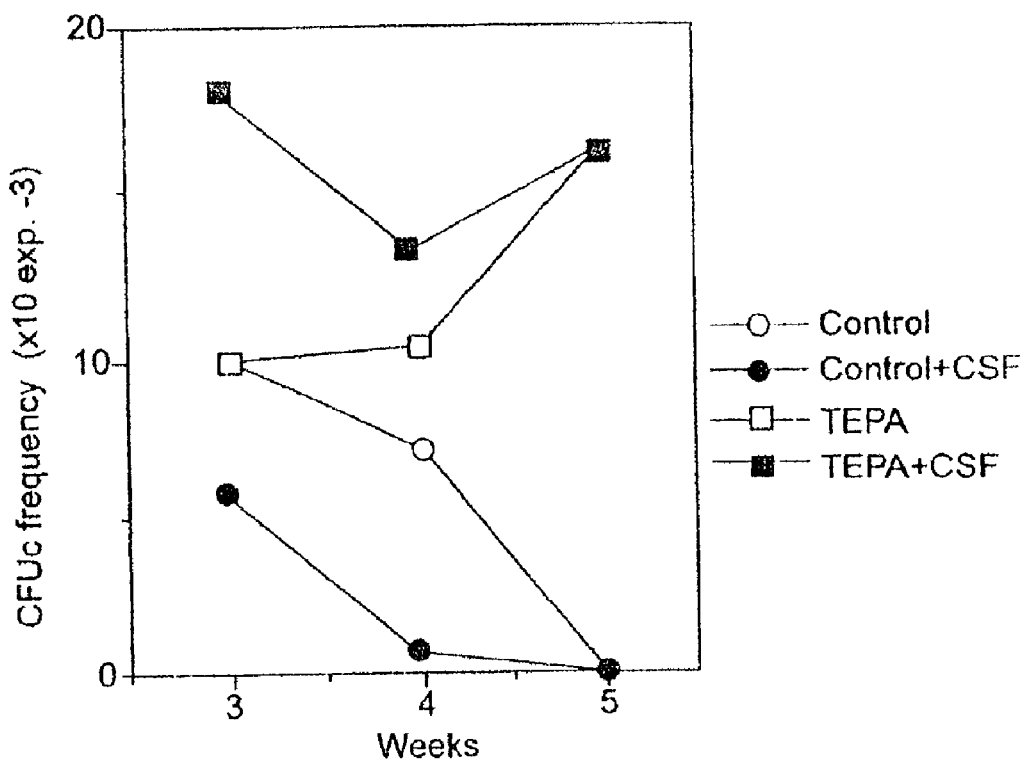
FIG. 15 shows the effect of G-CSF and GM-CSF on CFUc frequency of control and TEPA-supplemented $CD_{34}$ cultures. Cord blood-derived $CD_{34}$ cells were cultured as detailed in FIGS. 11a–c. After one week, half of the control and TEPA cultures were supplemented with the late-acting cytokines G-CSF and GM-CSF (10 ng/ml each). At weekly intervals, the cultures were demi-depopulated and supplemented with fresh medium, cytokines and TEPA. At weeks 3, 4 and 5, cells were counted, assayed for CFUc and CFUc frequency calculated.

FIG. 15 shows the effect of G-CSF and GM-CSF on CFUc frequency of control and TEPA-supplemented $CD_{34}$ cultures. Supplementing the cultures with the late-acting cytokines G-CSF and GM-CSF, which stimulate cell differentiation, resulted in rapid loss of clonogenic cells. This differentiation stimulatory effect is blocked by TEPA.

Figure 16:
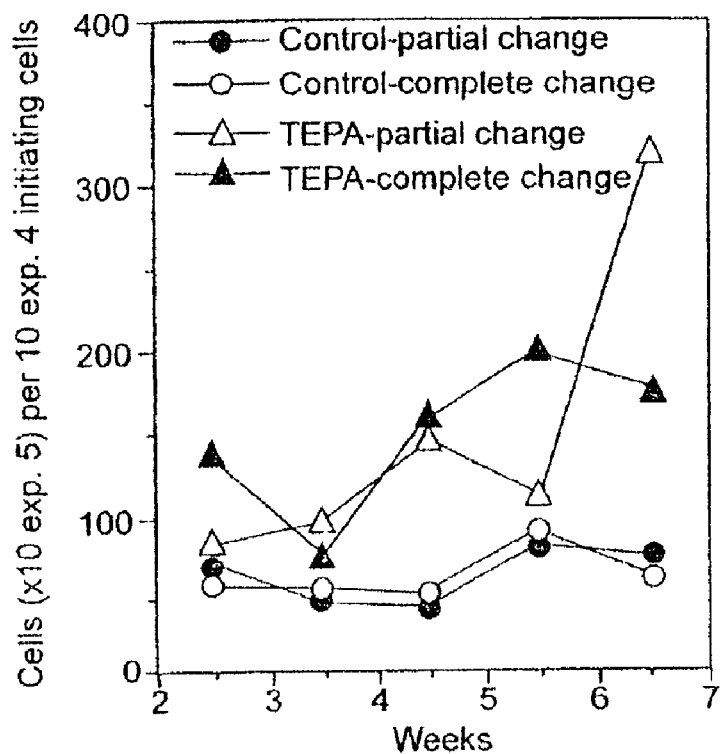
FIGS. 16–17 show the effect of partial or complete medium+TEPA change on long-term cell proliferation and CFUc production. Cord blood-derived $CD_{34}$ cells were cultured as detailed in FIGS 11a–c. At weekly intervals, the cultures were demi-depopulated and supplemented with fresh medium, cytokines and TEPA. At weekly intervals, half of the culture content (cells and supernatant) was removed and replaced by fresh medium, cytokines with or without TEPA (partial change). Alternatively, the whole content of the culture was harvested, centrifuged, the supernatant and half of the cells discarded and the remaining cells recultured in fresh medium, cytokines with or without TEPA (complete change). At the indicated weeks the number of cells (FIG. 16) and CFUc (FIG. 17) were determined.
Figure 17:
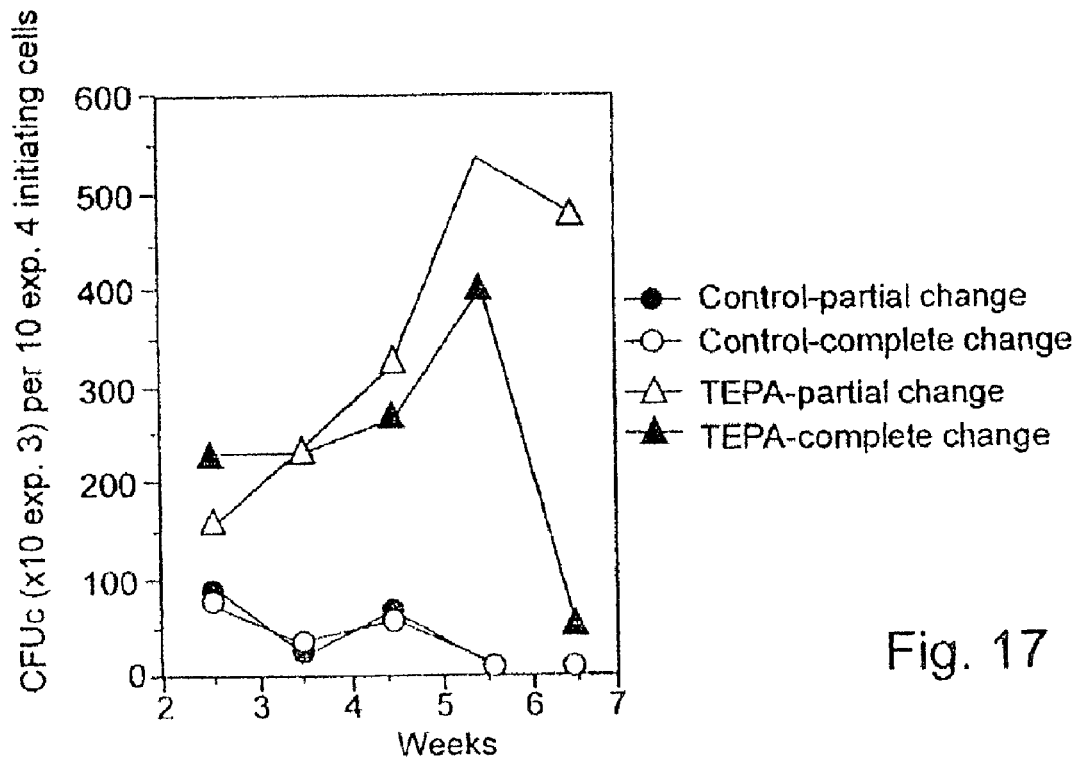

FIGS. 16–17 show the effect of partial or complete medium+TEPA change on long-term cell proliferation (FIG. 16) and CFUc production (FIG. 17). The results obtained indicate that for maintaining maximal expansion, TEPA should be completely replaced, at least, at weekly intervals.

Figure 19:
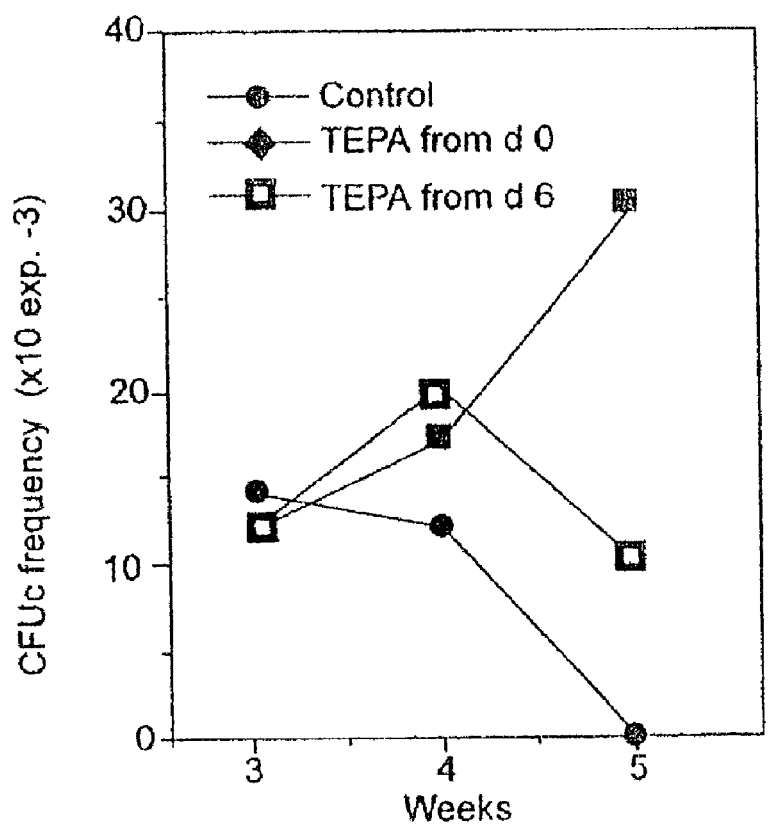
FIG. 19 shows the effect of delayed addition of TEPA on CFUc frequency. Cord blood-derived $CD_{34}$ cells were cultured as detailed in FIGS. 11a–c. TEPA (10 μM) was added at the initiation of the cultures (day 1) or 6 days later. At weekly intervals, the cultures were demi-depopulated and supplemented with fresh medium, cytokines and TEPA. At weeks 3, 4 and 5, cells were counted, assayed for CFUc and the CFUc frequency was calculated.

FIG. 19 shows the effect of delayed addition of TEPA on CFUc frequency. It is evident that early exposure of $CD_{34}$ cells to TEPA was crucial for long-term maintenance and expansion of CFUc, suggesting that TEPA affects differentiation of progenitors at various stages of differentiation.

Figure 20:
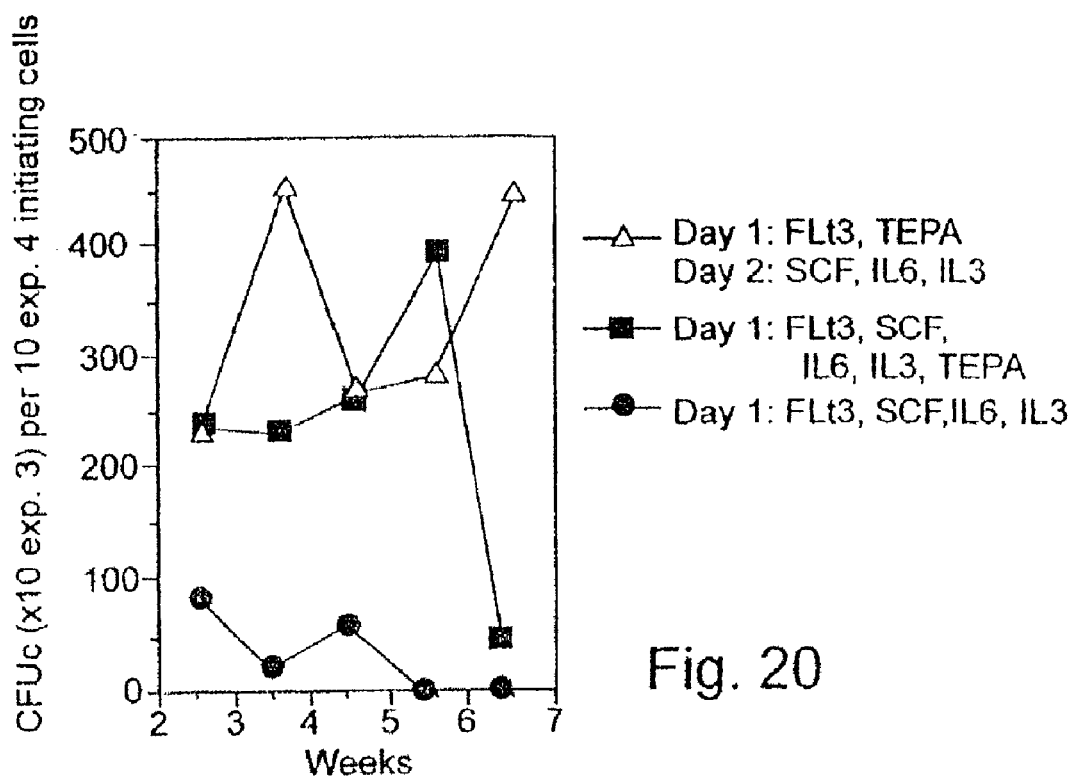
FIG. 20 show the effect of short-term preincubation with a single cytokine on long-term CFUc production. Cord blood-derived $CD_{34}$ cells were cultured as detailed in FIGS. 11a–c. Cultures were supplemented on day 1 with or without TEPA (10 μM) and with SCF, FLT3, IL-6, (50 ng/ml each) and IL-3 (20 ng/ml). Alternatively, cultures were supplemented on day 1 with TEPA (10 μM) and FLT3 (50 ng/ml) as a single cytokine. SCF, IL-6 (50 ng/ml each) and IL-3 (20 ng/ml) were added to these cultures at day 2. At weekly intervals, the cultures were demi-depopulated and supplemented with fresh medium, cytokines and TEPA. At the indicated weeks cells were assayed for CFUc.

FIG. 20 shows the effect of short-term preincubation with a single cytokine on long-term CFUc production. The results indicate that LTC-CFC are more preserved in TEPA-treated cultures when supplemented for the first 24 hours with a single cytokine rather than the full complement of cytokines, suggesting that under the former conditions cells are blocked more efficiently.

Figure 21A:
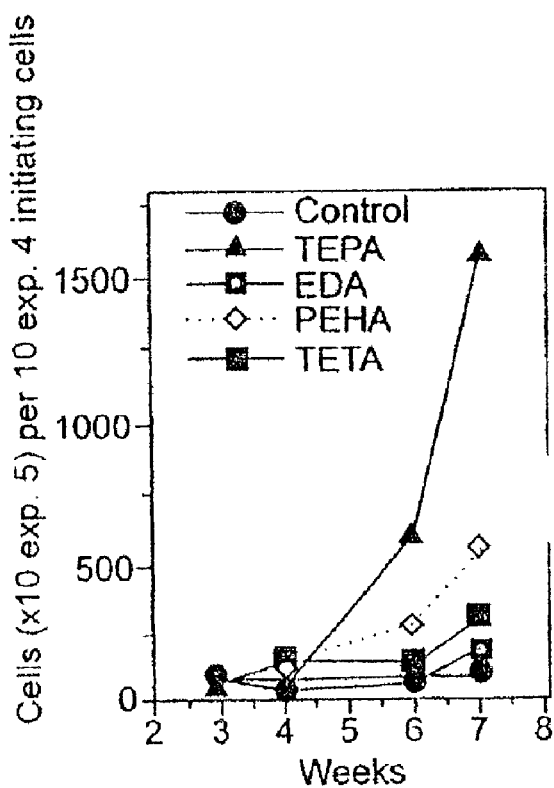
FIGS. 21a–b show the effect of polyamine chelating agents on $CD_{34}$ cell cultures. Cord blood-derived $CD_{34}$ cells were cultured as detailed in FIGS. 11a–c. The polyamine chelating agents tetraethylenepentamine (TEPA), pentaethylenehexamine (PEHA), ethylenediamine (EDA) or triethylene-tetramine (TETA) were added, at different concentrations. At weekly intervals, the cultures were demi-depopulated and supplemented with fresh medium, cytokines and chelators. At weeks 3, 4, 6 and 7, cells were counted and assayed for CFUc. The results presented are for concentrations with optimal activity: TEPA—40 μM, PEHA—40 μM, EDA—20 μM and TETA—20 μM.
Figure 21B:
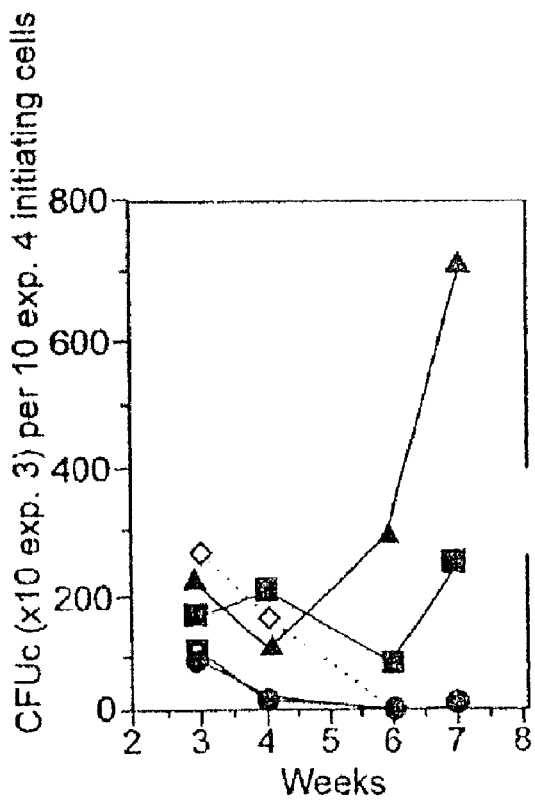

FIGS. 21a–b show the effect of polyamine chelating agents on $CD_{34}$ cell cultures. Polyamine chelating agents sustained cell proliferation and expanded CFUc during long term cultures. Among the compounds tested, the long-chain polyamines, TEPA and PEFIA, were found to be more effective than the short-chain polyamines.

Figure 22A:
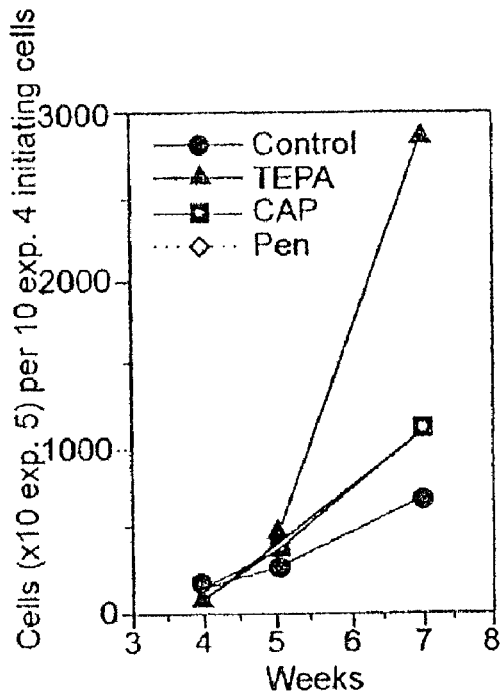
FIGS. 22a–b show the effect of transition metal chelating agents on $CD_{34}$ cell cultures. Cord blood-derived $CD_{34}$ cells were cultured as detailed in FIGS. 11a–c. The chelators Captopril (CAP), Penicilamine (PEN) and TEPA were added, at different concentrations. At weekly intervals, the cultures were demi-depopulated and supplemented with fresh medium, cytokines and chelators. At the weeks 4, 5 and 7, cells were counted and assayed for CFUc. The results presented are for concentrations with optimal activity: TEPA—10 μM, PEN—5 μM and CAP—40 μM.
Figure 22B:
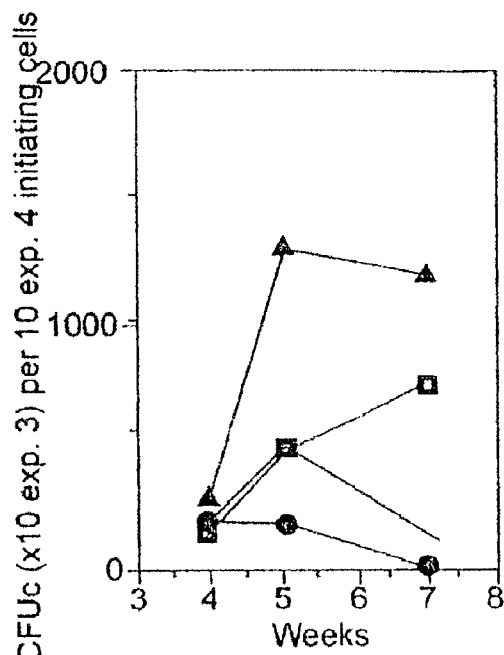

FIGS. 22a–b show the effect of transition metal chelating agents on $CD_{34}$ cell cultures. Penicilamine (PEN) and captopril (CAP), which are known transition metal chelators, sustained cell proliferation and expansion of clonogenic cells during long-term cultures.

Figure 23A:
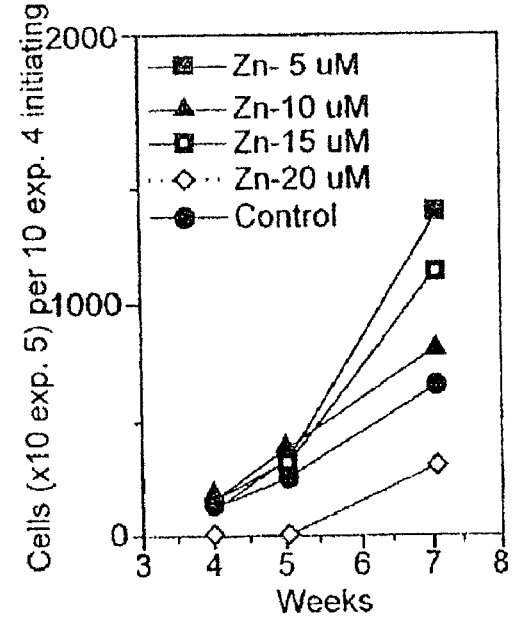
FIGS. 23a–b show the effect of Zinc on $CD_{34}$ cell cultures. Cord blood-derived $CD_{34}$ cells were cultured as detailed in FIGS. 11a–c. Zinc (Zn) was added, at different concentrations, on day 1. At weekly intervals, the cultures were demi-depopulated and supplemented with fresh medium, cytokines and Zn. At the weeks 4, 5 and 7, cells were counted and assayed for CFUc.
Figure 23B:
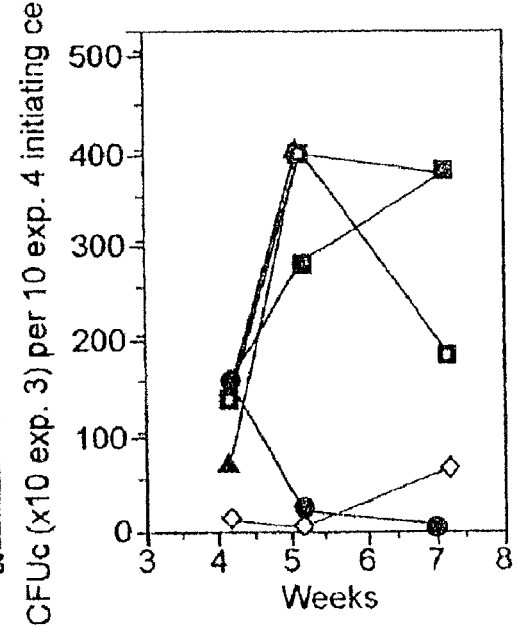
Figure 24:
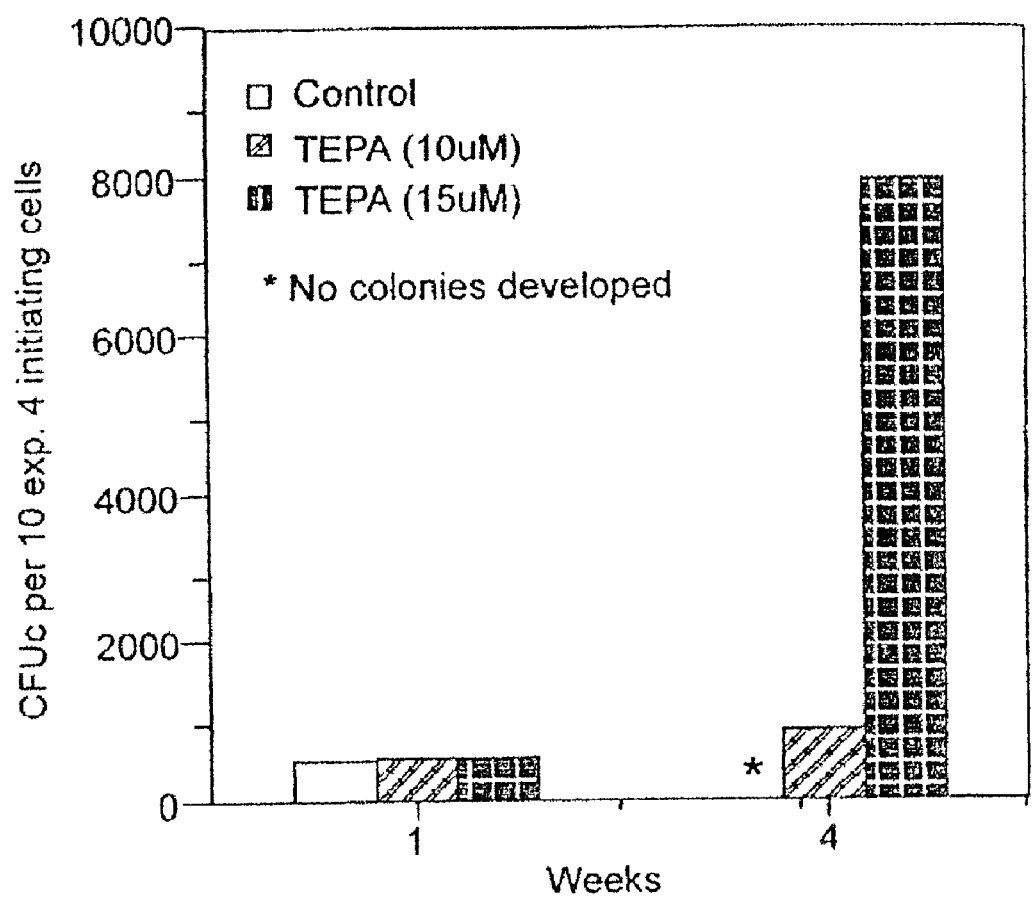
FIG. 24 shows the effect of TEPA on peripheral blood derived $CD_{34}$ cell cultures. Peripheral blood-derived $CD_{34}$ cells were cultured as detailed in FIGS. 11a–c. Cultures were supplemented with or without TEPA. At weekly intervals, the cultures were demi-depopulated and supplemented with fresh medium and TEPA. At weeks 1 and 4, and, cells were assayed for CFUc. * denotes that no colonies developed.

FIGS. 23a–b show the effect of Zinc on $CD_{34}$ cell cultures. Zinc, which is known to interfere with transition metal metabolism, Copper in particular, mimicked the effect of the chelating agents in long term cultures, but to a smaller extent than the chelators themselves.

Thus, ex-vivo expansion of hematopoietic progenitor cells is limited by the progression of these cells into non-dividing differentiated cells. This differentiation process can be delayed by cultivating the progenitor cells on stroma cell layer. Since the stroma supports continuous cell proliferation and long-term generation of CFUc, it is believed that the stroma inflict an anti differentiation effect on the progenitor cells.

According to another embodiment of the present invention there is provided a method of preservation of stem cells, such as, but not limited to, cord blood derived stem cells, peripheral blood derived stem cells and bone marrow-derived stem cells. The method is effected by handling the stem cell while being harvested, isolated and/or stored, in a presence of a transition metal chelator, e.g., TEPA.

Cord blood-derived cells were collected and stored (unseparated) for 24 hours, at 4° C., either in the presence or absence of 10 μM TEPA. $CD_{34}^+$ cells were then separated using either 10 μM TEPA-PBS buffer or TEPA free PBS buffer, respectively. Then, cells were grown in long-term cultures in the presence of 10 μM TEPA.

The results indicated that cultures which were initiated with cells that were handled in the presence of TEPA expanded for 8 weeks, whereas cultures initiated from cells stored without TEPA stopped expanding after 5 weeks only.

It is well known that it takes usually at least several hours between cell collection and either freezing or transplantation.

These results indicate that addition of a transition metal chelator, such as TEPA, to the collection bags and the separation and washing buffers increase the yield of stem cells and improve their potential for long-term growth, thus facilitate the short-term take and the long-term repopulation following transplantation of either "fresh", cryopreserved or ex-vivo expanded hematopoietic cells.

Thus, further according to the present invention there are provided stem cells collection bags and separation and washing buffers supplemented with an effective amount or concentration of transition metal chelator, which inhibits differentiation.

As is specifically demonstrated in the above examples, a novel system which sustains continuous cell proliferation and long-term generation of CFUc in stroma-free cultures (FIG. 11) has been developed. The system combines the use of early-acting cytokines, such as stem cell factor (SCF), FLT3, interleukin-6 (IL-6), thrombopoietin (TPO) with or without interleukin-3, and transition metal chelating agents (FIGS. 12–14). The early cytokines support the survival and proliferation of the progenitors with reduced stimulus for differentiation compared to late-acting cytokines, such as G-CSF and GM-CSF (FIG. 15). The chelators inhibit differentiation through chelation of transition metals, Copper in particular. Complete medium change at weekly intervals, as compared to partial change, improved LTC-CFC maintenance, suggesting that the TEPA-transition metal complex, e.g., TEPA-Copper complex, may not be stable (FIGS. 16–17).

Figure 18:
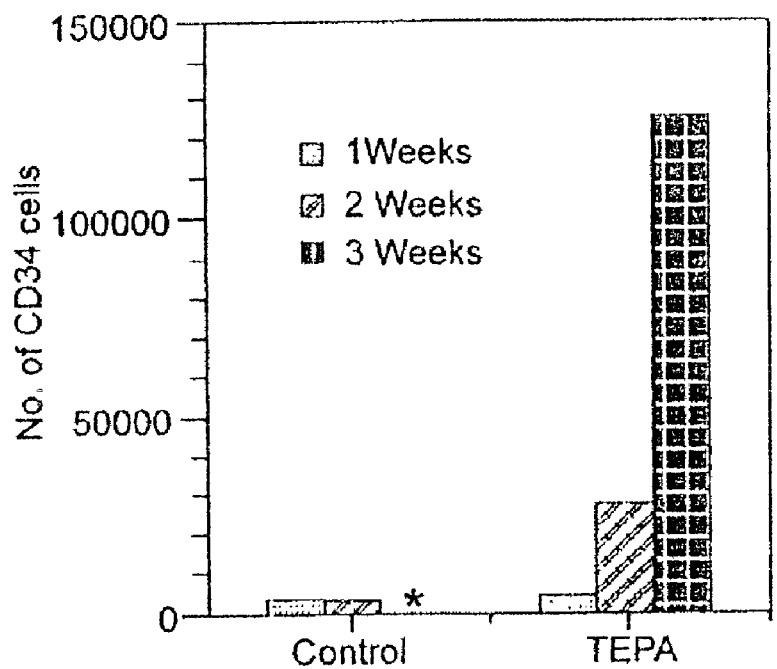
FIG. 18 show the effect of TEPA on $CD_{34}$ cell expansion. Cord blood-derived $CD_{34}$ cells were cultured as detailed in FIGS. 11a–c. At weeks 1, 2 and 3, $CD_{34}^+$ cells were enumerated by flow cytometry. * denotes that no colonies developed.

Several lines of evidence suggest that TEPA inhibits differentiation of early progenitors (FIG. 18). For example, when TEPA addition was delayed until day 6 of the culture its effects were reduced as compared to cultures supplemented with TEPA from day 1 (FIG. 19).

While optimal results were obtained when TEPA was added on day 1, it was advantageous to add the full complement of cytokines on day 2. Thus, TEPA-treated cultures which were supplemented for one day with only one cytokine, e.g., FLT3, followed by addition of the other cytokines (SCF, TPO and IL-3) were maintained longer than cultures where all the cytokines were added at day 1 (FIG. 20). We hypothesize that since cell differentiation is driven by the cytokines and is dependent on Copper and other transition metals, inhibition of differentiation requires depletion thereof prior to exposure to the full complement of cytokines. A single cytokine does not support rapid activation (proliferation and differentiation) but maintains cell viability, thus allowing TEPA to efficiently chelate transition metals in quiescent undifferentiated $CD_{34}$ cells prior to activation.

Following screening, various chelating agents have been found to support continuous cell proliferation and long-term generation of CFUc and to delay cell differentiation. Among them are the polyamines such as, but not limited to, TEPA, EDA, PEHA and TETA (FIGS. 21a–b) or chelators such as, but not limited to, penicilamine (PEN) and captopril (CAP) (FIGS. 22a–b). Zinc which interfere with transition metals (Copper in particular) metabolism also supported LTC-CFC (FIGS. 23a–b).

Example 2

The Effect of Copper-chelating Peptides on Proliferation and Clonability in $CD_{34}$ Cell Cultures Experimental Procedures $CD_{34}$ cells selection: Peripheral blood "buffy coat" cells derived from a whole blood unit, peripheral blood cells obtained following leukapheresis, or blood cells were layered on Ficoll-Hypaque (density 1.077 g/ml) and centrifuged at 1,000×g for 20 minutes at room temperature. The interphase layer of mononuclear cells were collected, washed three times with Ca/Mg free phosphate buffered saline containing 1% bovine serum albumin (BSA). The cells were incubated for 30 minutes at 4° C. with murine monoclonal anti $CD_{34}$ antibody (0.5 $\mu$g/$10^6$ monoclonal cells) and thereafter isolated using the miniMACA apparatus (Miltenyi-Biotec, Bergisch, Gladbach, Germany) according to the manufacturer's protocol.

Culture procedures: For the expansion of progenitor cells, $CD_{34}^+$ enriched fractions were seeded at $1\times10^4$ cells/ml in alpha minimal essential medium containing 10% preselected fetal calf serum (FCS) (both from GIBCO, Grand Island, N.Y.). The medium was supplemented with a mixture of growth factors and Copper chelators. The cultures were incubated at 37° C. in an atmosphere of 5% $CO_2$ in air with extra humidity. Half of the medium was changed weekly with fresh medium containing all the supplements.

The cloning potential of the cultured cells was assayed in semi-solid medium. The cells were washed and seeded in 35 mm dishes in methylcellulose containing alpha medium supplemented with 30% FCS and further with recombinant growth factors (stem cell factor (SCF), G-CSF, GM-CSF and erythropoietin (EPO)). Following two week incubation, the cultures were scored with an inverted microscope. Colonies were classified as blast, mixed, erythroid, myeloid, and megakaryocytic, according to their cellular composition.

Morphological assessment: In order to characterize the resulting culture populations, aliquots of cells were deposited on a glass slide (cytocentrifuge, Shandon, Runcorn, UK), fixed and stained in May-Grunwald Giemsa.

Immunofluorescence staining for $CD_{34}$ antigen: Cells were incubated on ice with FITC-labeled anti $CD_{45}$ monoclonal antibody and either phycoerythrin (PE)—labeled anti $CD_{34}$ (HPCA-2) monoclonal antibody or PE-labeled control mouse Immunoglobulins (Ig). After incubation, the cells were washed and analyzed by flow cytometry.

Flow cytometry: Cells were analyzed using FACStar$^{plus}$ flow cytometer (Becton-Dickinson, Immunofluorometry systems, Mountain View, Calif.). Cells were passed at a rate of 1,000 cells/second through a 70 $\mu$m nozzle, using saline as the sheath fluid. A 488 nm argon laser beam at 250 mW served as the light source for excitation. Green (FITC-derived) fluorescence was measured using a 530±30 nm band-pass filter and red (PE-derived) fluorescence—using a 575±26 nm band filter. The PMTs was set at the appropriate voltage. Logarithmic amplification was applied for measurements of fluorescence and linear amplification—for forward light scatter. At least $10^4$ cells were analyzed.

Experimental Results

The effect of Copper-chelating peptides on proliferation and clonability in $CD_{34}$ cell cultures: Cultures were initiated with $10^4$ cord blood-derived $CD_{34}+$ cells by plating purified cells in liquid medium in the presence of SCF, FLT3 and IL-6 (50 ng/ml each) and the Copper-binding peptides, Gly-Gly-His (GGH) or Gly-His-Lys (GHL) (10 $\mu$M each), or the late-acting cytokines G-CSF and GM-CSF (10 ng/ml each). At weekly intervals, the cultures were demi-depopulated and supplemented with fresh medium, cytokines and the peptides. After 7 weeks, cells were counted and assayed for CFUc.

Figure 25A:
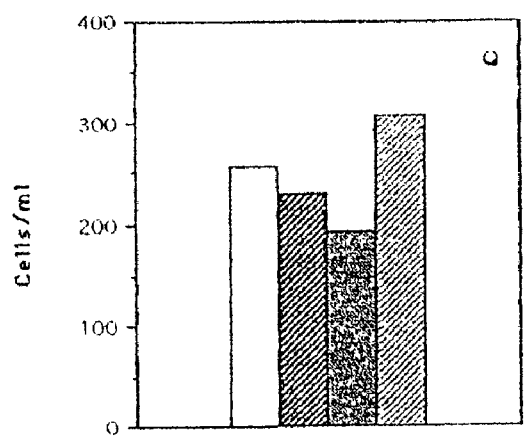
FIGS. 25a–b show the effect of Copper-chelating peptides on $CD_{34}^+$ cell cultures. Cultures were initiated with $10^4$ cord blood-derived $CD_{34}^+$ cells by plating purified cells in liquid medium in the presence of SCF, FLT3 and IL-6 (50 ng/ml each) and the Copper-binding peptides, Gly-Gly-His (GGH) or Gly-His-Lys (GHL) (10 μM each), or the late-acting cytokines granulocyte-CSF (G-CSF) and granulocyte macrophage-CSF (GM-CSF) (10 ng/ml each). At weekly intervals, the cultures were demi-depopulated and supplemented with fresh medium, cytokines and the peptides. After 7 weeks, cells were counted (FIG. 25a) and assayed for colony forming cells in culture (CFUc, FIG. 25b).
Figure 25B:
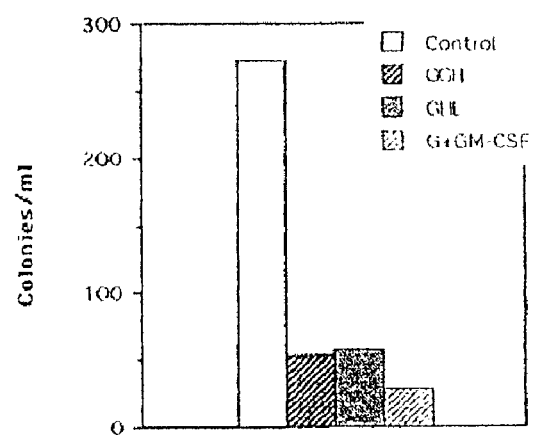

As shown in FIGS. 25a–b, the results indicated that GGH and GHL decreased cell number by 10% and 25%, respectively, and G-CSF+GM-CSF by 20%. The effect on the clonogenic potential of the cultures was much more pronounced: 80% and 78% decrease by GGH and GHL, respectively, and 89% by G-CSF+GM-CSF.

Example 3

Transition Metal Chelator Assay for Determining the Effect of a Specific Transition Metals Chelator on Cell Differentiation Experimental Procedures Inhibition of differentiation: MEL (mouse erythroleukemia cell line), $8\times10^3$ cells per ml were incubated for 24 hours with different chelators at concentrations indicated in Table 3 below. Then, cultures were supplemented with a differentiation inducer—hexamethylene bisacetamide, 2 mM. Number of cells and percentage of differentiated cells (benzidine positive) were determined 72 hours after addition of the inducer.

Similarly, HL-60 (human myeloid leukemia cell line), $1\times10^5$ cells per ml were incubated for 24 hours with different chelators at the concentrations indicated in Table 3 below. Then, cultures were supplemented with the differentiation inducers—vitamin D or retinoic acid (both at $1\times10^{-7}$ M). Number of cells and percentage of differentiated (phagocytosing) cells were determined.

Induction of differentiation: HL-60, $1\times10^5$ cells per ml were incubated with different chelators. Number of cells and percentage of differentiated (phagocytosing) cells were determined.

Copper Determination: Cells were harvested by centrifugation at 1000×g for 5 minutes. The cell pellet was washed three times by re-suspending the cells in PBS ($Ca^{++}$ and $Mg^{++}$ free) and centrifugation at 1000×g. An aliquot containing $2\times10^6$ cells was then transferred into a metal-free Eppendorf tube and the cells were recovered by centrifugation at 1000×g. The cell pellet was re-suspended in 0.03 M ultra-pure nitric acid to give a concentration of $1\times10^7$ cells/ml. The cells were homogenized with a high shear mixer (polytron, Kinematica, Switzerland) for 1 minutes to disrupt the cell and release intracellular copper content. Cell samples were vortexed before transferring to a vial autosampler and analyzed in duplicate by a Perkin Elmer graphite furnace atomic absorption spectrophotometer at a wavelength of 324.7 nm. The samples were analyzed against copper standard solution prepared from a commercial stock solution that was diluted with 0.03 M ultra pure nitric acid.

Experimental Results

Table 3 bellow summarized the results for HL-60 cells. Inhibition of differentiation of MEL cells yielded comparable results. FIG. 26 provides the chemical structure of the various chelators employed in these experiments.

for the effect of the chelators on various cell types such as the hematopoietic stem ($CD_{34+}$) cells.

Example 4

Modulation of Differentiation By Copper Chelators on Non-hematopoietic Cells

As is indicated in the Background section above, and as is known from the scientific literature, cooper depletion in-vivo affects a plurality of cell lineages, including, but hematopoietic cells. It was therefore anticipated that the effect of transition metal chelators on differentiation is not

TABLE 3

Positive correlation between the ability of copper chelators to inhibit or induce differentiation and copper content in chelator treated cells

| Compound Name | Copper Affinity (LogK Cu) | Differentiation Inhibition | | Induction | | growth inhibition | | Average Intracellular ppb Cu (% of control) | | | | | |
|---|---|---|---|---|---|---|---|---|---|---|---|---|---|
| Concentration tested | | 100 nM | 1000 nM | 100 nM | 1000 nM | 100 nM | 1000 nM | 20 µM | | 100 µM | | 500 µM | |
| Control | | | | | | | | | | 49 +− 18 | | | |
| N,N'-bis(3-amino-propyl)-1,3-propanediamine | 17.3 | − | − | − | − | − | − | 33.8 ppb | 69% | 26.2 ppb | 53% | 27.9 ppb | 57% |
| Triethylene tetramine | 20.2 | + | + | − | − | − | + | 27.7 ppb | 56% | 21.2 ppb | 43% | 16.8 ppb | 34% |
| N,N,Bis (2 animoethyl) 1,3 propane diamine | 23.9 | + | + | − | − | + | + | 10.8 ppb | 22% | 13.4 ppb | 27% | ND | |
| Tetraethylene pentamine (TEPA) | 24.3 | + | + | − | − | − | + | 31.5 ppb | 64% | 24.1 ppb | 49% | 17.1 ppb | 35% |
| Pentaethylene hexamine | | + | − | − | − | − | + | 19.3 ppb | 39% | 24.5 ppb | 50% | 17.2 ppb | 35% |
| 1,7-Dioxa-4,10-diazacyclodo-decane | | − | − | − | − | − | − | 35.5 ppb | 72% | 36.1 ppb | 73% | 35.0 ppb | 71% |
| 1,4,8,11-Tetraaza-cyclotetradecane-5,7-dione | 15 | − | − | − | − | − | − | 37.9 ppb | 77% | 27.4 ppb | 56% | 28.3 ppb | 57% |
| 1,4,7-Triazacyclononane trihydrochioride | 15.5 | + | + | − | − | − | − | 15.8 ppb | 32% | 17.7 ppb | 36% | ND | |
| 1-Oxa-4,7,10-triazacyclodode-cane | | + | + | − | − | − | − | 39.0 ppb | 79% | 22.9 ppb | 46% | 17.6 ppb | 36% |
| 1,4,8,12-tetraaza-cyclopentadecane | 24.4 | + | + | − | − | + | + | 13.4 ppb | 27% | 12.1 ppb | 25% | 9.6 ppb | 19% |
| 1,4,7,10-Tetraaza-cyclododecane | 24.8 | − | − | + | Toxic | | | 27.5 ppb | 56% | 73.9 ppb | 150% | Toxic | |
| 1,4,8,11-Tetraaza-cyclotetradecane | 27.2 | + | + | − | − | + | + | 15.0 ppb | 30% | 11.4 ppb | 23% | 19.9 ppb | 40% |
| Glycyl-glycyl-histidine Cu complex (GGH—Cu) | | − | − | + | + | + | + | 202.7 ppb | 411% | 582 ppb | 1181% | 1278 ppb | 2592% |
| Glycyl-histidyl-lysine Cu complex (GHK—Cu) | | − | − | + | + | + | + | 481 ppb | 976% | 473 ppb | 959 | 1066 ppb | 2162% |

ND—not determined;
ppb—parts per billion.

As is evident from Table 3 above, good correlation was found between the ability of chelators to modulate cellular copper content and their biological activities. Chelators that reduce cellular copper content are potent differentiation inhibitors. On the other hand, chelators that increase cellular copper content are potent differentiation inducers. Indeed, differentiation inhibitory chelators, such as TEPA, PEHA etc., when tested for their activity on $CD_{34+}$ cells, were found to inhibit differentiation. Chelators with differentiation inducing activity such as 1,4,7,10-Tetra-azacyclododecane and the copper binding peptides GGH and HHK were found to stimulate differentiation. Therefore, screening for the ability of chelators to modulate (increase or decrease) cellular copper content could be a predictive assay limited to cells of the hematpoietic lineage, rather this effect is an underlying phenomenon shared by all eukaryotic cells.

Embryonal stem cells: Embryonal stem cells can be maintained undifferentiated in culture when the medium is supplemented with Leukemia Inhibitory Factor (LIF). It was found that TEPA can replace LIF in maintaining the undifferentiative phenotype of the cells.

Thus, embryonal stem cells were cultured for 3–4 days essentially as described in (66), in the presence of LIF (20–100 ng/ml) or TEPA (10–20 µM) and their differentiation compared to non-treated control cells.

TABLE 4

The effect of TEPA of embryonal stem cells

| Compound added | Effect on | |
|---|---|---|
| | Differentiation | Proliferation |
| Control | + | +/− |
| LIF | − | + |
| TEPA | − | + |

The results presented in Table 4, clearly indicate that TEPA exerts a similar effect on embryonal stem cells as it does for other cell types.

Figure 27A:
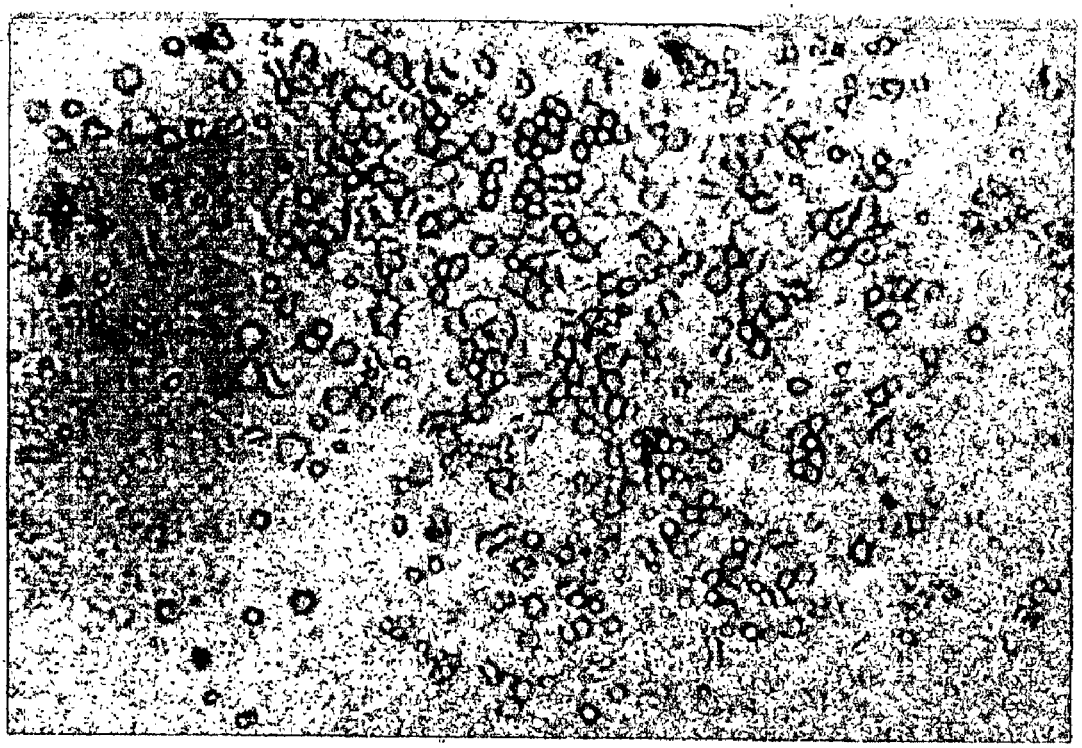
FIGS. 27a–f show photographs of hepatocytes cultures that were ex-vivo expanded with (27a–d) or without (27e–f) TEPA for five weeks.
Figure 27B:
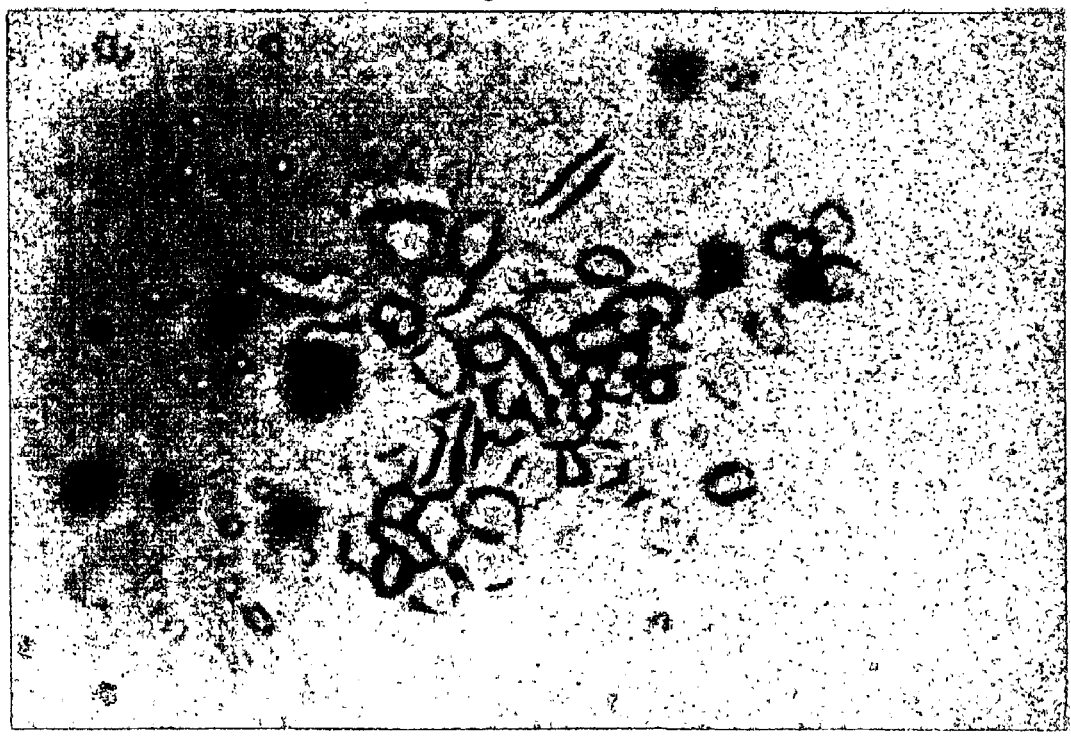
Figure 27C:
Figure 27D:
Figure 27E:
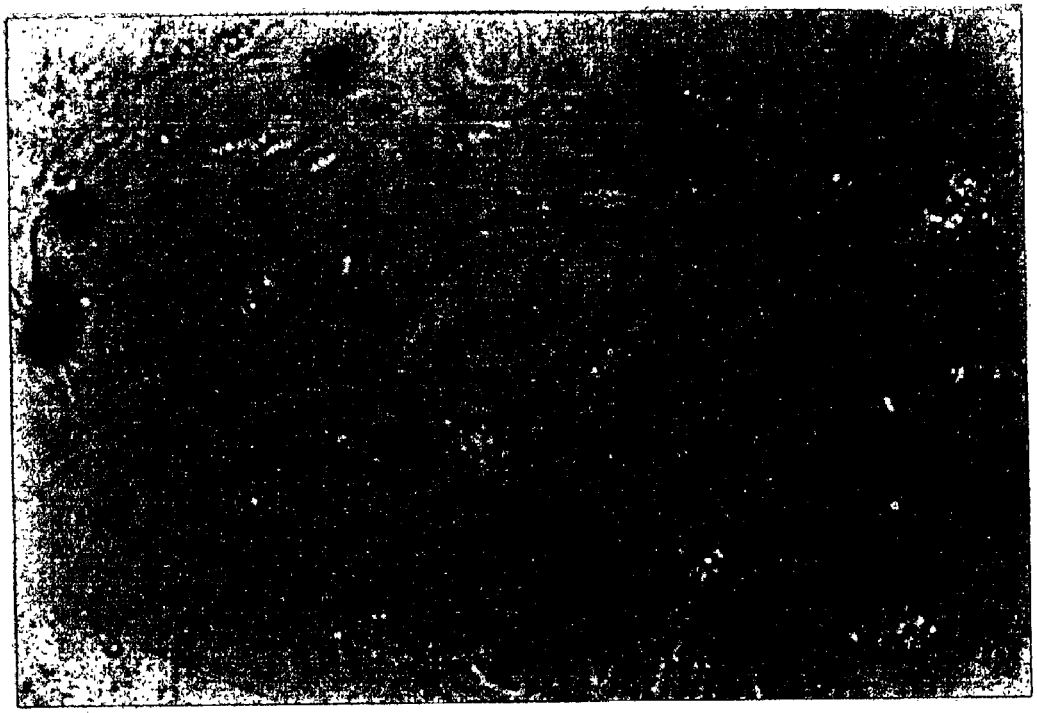
Figure 27F:

Hepatocytes: Livers were dissected from anesthetized BALB/c mice with sterile tools and immersed into F12 culture medium (Biological Industries, Kibbutz Bet Ha'Emek, Israel). The livers were washed three times with 3% BSA/PBS buffer and minced into small pieces with seizures. Following three washes with 3% BSA/PBS the liver tissue pieces were incubated for 30 minutes with 0.05% collagenase at 37° C. with continues shaking under 5% $CO_2$ atmosphere. The digested liver tissue pieces were than mashed by pressing through a fine mesh strainer. After three washes with 3% BSA/PBS the liver cells were seeded into F12 culture medium enriched with: 15 mM HEPES buffer, 0.1 glucose, 10 mM sodium bicarbonate, 0.5 u/ml insulin, 7.5 ng/ml hydrocortisone and with or without 15 μg/ml of TEPA and incubated at 37° C. in a 5% $CO_2$ atmosphere. After overnight incubation the medium was removed and the cells were supplemented with fresh enriched F12 medium as described above with or without 15 μg/ml of TEPA. Hepatocytes were incubated in 35 mm dishes for several weeks with enriched F12 culture medium with or without 15 μg/ml TEPA at 37° C. under 5% $CO_2$ atmosphere. Cell culture medium was replaced every week with a fresh medium. Hepatocytes cultures that were ex-vivo expanded with TEPA for five weeks contained many dividing and undifferentiated cells (FIGS. 27a–d), while cultures that were not treated with TEPA contained a very small amount of only differentiated cells (FIGS. 27e–f).

Plant cells: The effect of TEPA on the intracellular copper content of plant cells was determined as follows. Boston fern Callus tissue cultures were obtained from a commercial plant tissue culture production facility (Biological Industries, Kibbutz Bet Ha'Emek, Israel) and incubated with different concentrations of TEPA in the culture medium for two days at room temperature.

After three washes with PBS the tissues were suspended in 0.03 M ultra pure nitric acid and homogenized with a high shear mixer (polytron, Kinematica, Switzerland) for 3 minutes to disrupt the cells and release intracellular copper. Cell samples were vortexed before transferring to a vial autosampler and analyzed in duplicate by a Perkin Elmer graphite furnace atomic absorption spectrophotometer at a wavelength of 324.7 nm. The samples were analyzed against copper standard solution prepared from a commercial stock solution that was diluted with 0.03 M ultra pure nitric acid.

Table 5 below summarizes the effect of different TEPA concentration in the growth medium on the intracellular copper concentration of plant cells.

TABLE 5

Effect of different TEPA concentration in the growth medium on the intracellular copper concentration of plant callus tissues

| TEPA Concentration in Medium | Average Intracellular Copper Content (ppb) |
|---|---|
| 0 μM (Control) | 36.85 +/− 16.0 |
| 10 μM | 13.85 +/− 4.09 |
| 50 μM | 8.45 +/− 0.05 |
| 100 μM | 7.1 +/− 2.12 |

It is evident from Table 5 above that incubation of plant cells with TEPA causes a reduction of the intracellular content of copper in the cells.

Example 5

Evaluation of the In-vivo Potential of Ex-vivo Cultured Cells

Engraftment of SCID mice by ex-vivo expanded human hematopoietic cells: Cord blood purified $CD_{34+}$ cells either fresh or following 2 or 4 weeks of ex-vivo culture (plus or minus TEPA) were injected into NOD/SCID mice essentially as described in (56). After 4 weeks, the mice were sacrificed and their femora and tibias were excised and the bone marrow flushed with a syringe fitted with a 25 gauge needle. A single cell suspension was prepared, the cells were washed and an aliquot counted with Trypan blue.

In order to quantitate engrafted cells of human origin, cells were stained with FITC-conjugated anti $CD_{45}$ antibodies and PE-conjugated either anti $CD_{34}$, $CD_{19}$ or $CD_{33}$ antibodies. Anti $CD_{45}$ antibodies recognize human, but not mouse, cells, and thus, indicates the human origin of the cells.

The proliferation and differentiation potential of the engrafted cells was assayed by cloning bone marrow cells in semi-solid medium under conditions that allow specifically growth of human derived colonies essentially as described in (56).

The results (Table 6) indicate that the engraftment potential of expanded cells is higher than that of fresh cells, 20–60% $CD_{45+}$ as compared to 3–6% $CD_{45+}$ cells, respectively. All 6 cord blood samples that were expanded ex-vivo in the presence of TEPA succeeded to engraft the animals, whereas only 2 out of 6 samples that were expanded without TEPA engrafted.

TABLE 6

| | Ex-vivo | | +Engraftment | | | |
|---|---|---|---|---|---|---|
| | Weeks | Treatment | $CD_{45}$ (%) | $CD_{34}$ (%) | $CD_{19}$ (%) | *Colonies |
| CB 2 10% FCS | 0 | — | 4 | 1.6 | 1.7 | 100 |
| | 2 | Cytokines | 40 | 11 | 15 | 260 |
| | 2 | TEPA + Cytokines | 56 | 13 | 11 | 330 |
| CB 2 10% FCS | 0 | — | 3 | 1.2 | 1.5 | 70 |
| " | 2 | Cytokines | 38 | 5.7 | 14 | 127 |
| " | 2 | TEPA + Cytokines | 48 | 13.5 | 9 | 528 |
| CB 3 10% FCS | 0 | — | 4 | 1.8 | 2.2 | 250 |
| " | 2 | Cytokines | 0 | 0 | 0 | 0 |
| " | 2 | TEPA + Cytokines | 20 | 4 | 5 | 100 |
| CB 4 1% FCS | 2 | Cytokines | 5 | 1 | 0.7 | 4 |
| " | 2 | TEPA + Cytokines | 28 | 7 | 8 | 185 |
| " | 4 | Cytokmes | 4 | 2 | 3 | 4 |
| " | 4 | TEPA + Cytokines | 40 | 9 | 14 | 267 |
| CB 5-FCS | 4 | Cytokines | 4.7 | 1.6 | 1 | 5 |
| " | 4 | TEPA + Cytokines | 21 | 6 | 9 | 275 |
| CB 6 10% FCS | 2 | Cytokines | died | died | died | died |
| " | 2 | TEPA + Cytokines | 73 | 9 | 26 | 420 |
| CB 6 1% FCS | 2 | Cytokines | 6 | 4 | 6 | 8 |
| " | 2 | TEPA + Cytokines | 73 | 16 | 19 | 350 |

No. of cells transplanted per mouse: Fresh CB = $1 \times 10^5$ purified $CD_{34+}$ cells; Ex-vivo expanded = the yield of $1 \times 10^5$ (CB1-4,6) or $0.5 \times 10^5$ (CB5) cultured CB $CD_{34}^+$ cells.
*No. of colonies (erythroid and myeloid) per $2 \times 10^5$ SCID BM cells.
Human neonatal cord blood.
+Mean of 2–3 mice.

Hematopoietic reconstitution of lethally irradiated mice—fresh vs. ex-vivo expanded cells: Three month old female Balb/c×C57B1/6 F1 mice were lethally irradiated (1000 rad) and transplanted one day later with $1 \times 10^5$ fresh bone marrow cells or the yield of $1 \times 10^5$ bone marrow cells expanded ex-vivo either with or without TEPA for 3 to 5 weeks, as detailed in Table 7. Peripheral blood WBC counts were performed on weekly basis.

The results indicated that WWBC recovery was faster in mice transplanted with bone marrow cells expanded ex-vivo in the presence of TEPA as compared to fresh or cells expanded without TEPA.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

List of References Cited

1. Van Epps D E, et al. Harvesting, characterization, and culture of $CD_{34}$+ cells from human bone marrow, peripheral blood, and cord blood. Blood Cells 20:411, 1994.

TABLE 7

| | | | WBC × $10^6$/ml | | | Survival | | |
|---|---|---|---|---|---|---|---|---|
| | | | | Ex-vivo expansion with | | | Ex-vivo expansion with | |
| | Ex-vivo (Weeks) | In-vivo (Days) | Fresh BM | cytokines | TEPA + cytokines | Fresh BM | cytokines | TEPA + cytokines |
| Exp. I | 3 | 13 | 0.3 | 0.5 | 0.7 | 4/5 | 4/5 | 5/5 |
| | 3 | 19 | 0.48 | 0.58 | 1.5 | 4/5 | 4/5 | 5/5 |
| Exp. II | 3 | 11 | 0.17 | 0.07 | 0.92 | 5/5 | 4/5 | 5/5 |
| | 3 | 29 | 5.6 | 0 | 10.8 | 5/5 | 0/5 | 5/5 |
| Exp. III | 5 | 6 | 0.1 | 0.02 | 0.69 | 5/5 | 5/5 | 5/5 |
| | 5 | 11 | 0.21 | 0.23 | 1.27 | 3/5 | 5/5 | 5/5 |
| | 5 | 19 | n.d. | n.d. | n.d. | 3/5 | 2/5 | 4/5 |
| | 5 | 27 | n.d. | n.d. | n.d. | 3/5 | 1/5 | 4/5 |

No. of cells transplanted per mouse:
Fresh BM = $1 \times 10^5$ cells.
Ex-vivo expansion = the yield of $1 \times 10^5$ cultured BM cells.
Survival of irradiated mice that were not transplanted was 0/5 in all three experiments.

2. Emerson S G. Ex-vivo expansion of hematopoietic precursors, progenitors, and stem cells: The next generation of cellular therapeutics. Blood 87:3082, 1996.
3. Brugger W, et al. Reconstitution of hematopoiesis after high-dose chematotherapy by autologus progenitor cells generated in-vivo. N Engl J Med 333:283, 1995.
4. Williams S F, et al. Selection and expansion of peripheral blood $CD_{34}+$ cells in autologous stem cell transplantation for breast cancer. Blood 87:1687, 1996.
5. Zimmerman R M, et al. Large-scale selection of $CD_{34}+$ peripheral blood progenitors and expansion of neutrophil precursors for clinical applications. J Heamatotherapy 5:247, 1996.
6. Koller M R, Emerson S G, Palsson B O. Large-scale expansion of human stem and progenitor cells from bone marrow mononuclear cells in continuous perfusion cultures. Blood 82:378, 1993.
7. Lebkowski J S, et al. Rapid isolation and serum-free expansion of human $CD_{34}+$ cells. Blood Cells 20:404, 1994.
8. Sandstrom C E, et al. Effects of $CD_{34}+$ cell selection and perfusion on ex-vivo expansion of peripheral blood mononuclear cells. Blood 86:958, 1995.
9. Eiprs P G, et al. Retroviral infection of primitive hematopoietic cells in continuous perfusion culture. Blood 86:3754, 1995.
10. Freedman A R, et al. Generation of T lymphocytes from bone marrow $CD_{34}+$ cells in-vitro. Nature Medicine 2:46, 1996.
11. Heslop H E, et al. Long term restoration of immunity against Epstein-Barr virus infection by adoptive transfer of gene-modified virus-specific T lymphocytes. Nature Medicine 2:551, 1996.
12. Protti M P, et al. Particulate naturally processed peptides prime a cytotoxic response against human melanoma in-vitro. Cancer Res 56:1210, 1996.
13. Rosenberg S A, et al. Prospective randomized trial of high-dose interleukin-2 alone or in conjunction with lymphokine-activated killer cells for the treatment of patients with advanced cancer. J Natl Cancer Inst 85: 622, 1993.
14. Bernhard H, et al. Generation of immunostimulatory dendritic cells from human $CD_{34}+$ hematopoietic progenitor cells of the bone marrow and peripheral blood. Cancer Res 1099, 1995.
15. Fisch P, et al. Generation of antigen-presenting cells for soluble protein antigens ex-vivo from peripheral blood $CD_{34}+$ hematopoietic progenitor cells in cancer patients. Eur J Immunol 26:595, 1996.
16. Siena S, et al. Massive ex-vivo generation of functional dendritic cells from mobilized $CD_{34}+$ blood progenitors for anticancer therapy. Expt Hematol 23:1463, 1996.
17. Petzer A L, Zandstra P W, Piret J M, Eaves C J. Differential cytokine effects on primitive ($CD_{34}+CD38-$) human hematopoietic cells: novel responses to FIT3—ligand and thrombopoietin. J Exp Med 183:2551, 1996.
18. Schwartz R M, et al. In-vitro myelopoiesis stimulated by rapid medium exchange and supplementation with hematopoietic growth factors. Blood 78:3155, 1991.
19. Verfaillie C M. Can human hematopoietic stem cells be cultured in-vivo? Stem Cells 12:466, 1994.
20. Haylock D N, et al. Ex-vivo expansion and maturation of peripheral blood $CD_{34}+$ cells into the myeloid lineage. Blood 80:1405, 1992.
21. Brugger W, et al. Ex-vivo expansion of enriched peripheral blood $CD_{34}+$ progenitor cells by stem cell factor, interleukin-1 beta (IL-1 beta), IL-6, IL-3, interferon-gamma, and erythropoietin. Blood 81:2579, 1993.
22. Sato N, et al. In-vitro expansion of human peripheral blood $CD_{34}+$ cells. Blood 82:3600, 1993.
23. Fibach E, Manor D, Oppenheim A, Rachmilewitz E A. Proliferation and maturation of human erythroid progenitors in liquid medium. Blood 73:100, 1989.
24. Fibach E, Manor D, Treves A, Rachmilewitz E A. Growth of human normal erythroid progenitors in liquid culture: A comparison with colony growth in semisolid culture. Internatl J Cell Clon 9:57, 1991.
25. Fibach E, Rachmilewitz E A. The two-step liquid culture—novel procedure for studying maturation of human normal and pathologic erythroid precursors. Stem Cells 11:36, 1993.
26. Dalyot N, Fibach E, Rachmilewitz E, Oppenheim A. Adult and neonatal patterns of human globin gene expression are recapitulated in liquid cultures. Exper Hematol 20:1141, 1992.
27. Banno S, et al. Anemia and neutropenia in elderly patients caused by copper deficiency for long-term eternal nutrition. Rinsho-ketsueki 35:1276, 1994.
28. Wasa M, et al. Copper deficiency with pancytopenia during total parenteral nutrition. JPEN J Parenter Enteral Nutr 18:190, 1994.
29. Zidar B L, Shadduck R K, Zeigler Z, Winkelstein A. Observation on the anemia and neutropenia of human copper deficiency. Am J Hematol 3:177, 1977.
30. Hirase N, et al. Anemia and neutropenia in a case of copper deficiency: Role of copper in normal hematopoiesis. Acta Haematol 87:195, 1992.
31. Percival S S, Layden-Patrice M. HL-60 cells can be made copper deficient by incubating with tetraethylenepentamine. J Nutr 122:2424, 1992.
32. Percival S S. Neutropenia caused by copper deficiency: possible mechanisms of action. Nutr Rev 53:59, 1995.
33. Bae B, Percival S S. Retinoic acid-induced HL-60 cell differentiation is augmented by copper supplementation. J Nutr 123:997, 1993.
34. Bae B, Percival S S. Copper uptake and intracellular distribution during retinoic acid-induced differentiation of HL-60 cells. J Nutr Biochem 5:457, 1994.
35. Alter B P. Fetal erythropoiesis in stress hemopoiesis. Experimental Hematology 7:200, 1979.
36. Repair of myelin disease: Strategies and progress in animal models. Molecular Medicine Today. Dec. 1997. pp. 554–561.
37. Blau C A et al. Fetal hemoglobin in acute and chronic stage of erythroid expansion. Blood 81:227, 1993.
38. Schechtez A N et al. Sickle cell anemia. In: Molecular basis of blood diseases. Stamatoyannaopoulos G, Nienhuis A W, Leder P and Majerus P W Eds. pp. 179–218, Sounders Philadelphia.
39. Ross J W and Frant M S. Chelometric indicators, titration with the solid state cupric ion selective electrode. Analytical Chemistry 41:1900, 1969.
40. Fosmire G J. Zinc toxicity. Am J Clin Nutr 51 (2): 225–227, 1990.
41. Simon S R, et al. Copper deficiency and siberoblastic anemia associated with zinc ingestion. Am J Hematol 28(3): 181–183, 1988.
42. Hoffman H N 2d, et al. Zinc-induced copper deficiency. Gastroenterology 94(2): 508–512, 1988.
43. Reeves P G, et al. High zinc concentrations in culture media affect copper uptake and transport in differentiated human colon adenocarcinoma cells. J Nutr 126(6): 1701–1712, 1996.
44. Tashiro Itoh T, et al. Metallothionein expression and concentrations of copper and zinc are associated with tumor differentiation in hepatocellular carcinoma. Liver 17(6): 300–306, 1997.
45. Cable E E, Isom H C. Exposure of primary rat hepatocytes in long-term DMSO culture to selected transition metals induces hepatocyte proliferation and formation of duct-like structures. Hepatology 26(6): 1444–1457, 1997.
46. Kizaki M, et al. Regulation of manganese superoxide dismutase and other antioxidant genes in normal and leukemic hematopoietic cells and their relationship to cytotoxicity by tumor necrosis factor. Blood 82(4): 1142–1150, 1993.
47. Brugnera E, et al. Cloning, chromosomal mapping and charatcerization of the human metal-regulatory transcription factor MTF-1. Nucleic Acids Res 22(15): 3167–3173, 1994.
53. Kim H, Lipscomb W N. Differentiation and identification of the two catalytic metal binding sites in bovine lens leucine aminopeptidase by x-ray crystallography. Proc Natl Acad Sci USA 90(11): 5006–5010, 1993.
54. Fibach, E., Landau, T & Sachs, L. Normal differentiation of myeloid leukemic cells induced by differentiation indicing protein, nature 237:276–8, 1972.
55. Rosenberg S A, et al. Prospective randomized trial of high-done IEZ alone or in conduction with lymphokie activated Kilher cells for the treatment of particular with advanced cancer. *J. Natl. Cancer Inst.* 85; 622, 1993.
56. Lapidot, T., Pflumio, F., Doedens, M., Murdoch, B., Williams. D. E., Dick, J. E. Cytokine stimulation of multilineage hematopoiesis from immature human cells engrafted in SCID mice. *Science* 255:1137–41, 1992.

SEQUENCE LISTING

```
<160> NUMBER OF SEQ ID NOS: 2

<210> SEQ ID NO 1
<211> LENGTH: 3
<212> TYPE: PRT
<213> ORGANISM: Artificial Sequence
<220> FEATURE:
<223> OTHER INFORMATION: synthetic peptide

<400> SEQUENCE: 1

Gly His Lys
1

<210> SEQ ID NO 2
<211> LENGTH: 3
<212> TYPE: PRT
<213> ORGANISM: Artificial Sequence
<220> FEATURE:
<223> OTHER INFORMATION: synthetic peptide

<400> SEQUENCE: 2

Gly Gly His
1
```

48. Heuchel R, et al. The transcription factor MTF-1 is essential for basal and heavy metal-induced metallothionein gene expression. Embo J 13(12): 2870–2875, 1994.
49. Palmiter R D. Regulation of metallothionein genes by heavy metals appears to be mediated by a zinc-sensitive inhibitor that interacts with a constitutively active transcription factor, MTF-1. Proc Natl Acad Sci USA 91(4): 1219–1223, 1994.
50. Hatayama T, et al. Regulation of hsp70 synthesis induced by cupric sulfate and zinc sulfate in thermotolerant HeLa cells. J Biochem Tokyo 114(4): 592–597, 1993.
51. Filvaroff E, et al. Functional evidence for an extracellular calcium receptor mechanism triggering tyrosine kinase activation associated with mouse keratinocyte differentiation. J Biol Chem 269(34):21735–21740, 1994.
52. Okazaki T, et al. Characteristics and partial purification of a novel cytosolic, magnesium-independent, neutral sphingomyelinase activated in the early signal genetic modification of a 1 alpha, 25-dihydroxyvitamin D3-induced HL-60 cell differentiation. J Biol Chem 269 (6): 4070–4077, 1994.]

What is claimed is:

1. An expanded undifferentiated hematopoietic cell population having reduced intracellular cooper content obtained by ex vivo culturing of seeded hematopoietic cells in a culture medium providing said hematopoietic cells with conditions for cell proliferation and in the presence of a transition metal chelator having an affinity for copper,
wherein said chelator and said proliferation conditions result in (i) prolonged active hematopoietic cell proliferation; (ii) prolonged expansion of clonogenic cells; and (iii) maintenance of undifferentiated hematopoietic cells in their undifferentiated state,
thereby inhibiting differentiation while permitting expansion of said hematopoietic cell population in said culture medium,
and wherein said hematopoietic cells are hence expanded yet not further differentiated as compared to ex vivo seeded hematopoietic cells from which said expanded hematopoietic cell population expanded.

2. The expanded hematopoictic cell population of claim 1, wherein said cells are provided in said medium.

3. The expanded hematopoietic cell population of claim 1, wherein said cells are isolated from said medium.

4. A pharmaceutical composition comprising the expanded hematopoietic cell population of claim 1.

5. A pharmaceutical composition comprising the expanded hematopoietic cell population of claim 3.

6. The expanded hematopoietic cell population of claim 1, wherein said seeded cells are enriched for committed progenitor hematopoietic cells.

7. The expanded hematopoietic cell population of claim 1, wherein said hematopoietic cells are derived from neonatal umbilical cord blood.

8. The expanded hematopoietic cell population of claim 1, wherein said transition metal chelator is tetraethylenepentamine.

9. The expanded hematopoietic cell population of claim 1, wherein said culture medium comprises nutrients and a cytokine or cytokines.

10. The expanded hematopoietic cell population of claim 9, wherein said cytokine or cytokines is an early acting cytokine or cytokines.

11. The expanded hematopoietic cell population of claim 10, wherein said early acting cytokine is FLT3 ligand.

12. The expanded hematopoietic cell population of claim 9, wherein said cytokine or cytokines is a late acting cytokine or cytokines.

13. The expanded hematopoietic cell population of claim 12, wherein said late acting cytokine is granulocyte colony stimulating factor.

14. The expanded hematopoietic cell population of claim 8, wherein said transition metal chelator concentration is about 0.1 $\mu$M to about 100 mM.

15. The expanded hematopoietic cell population of claim 14, wherein said transition metal chelator concentration is about 4 $\mu$M to about 50 mM.

16. The expanded hematopoietic cell of claim 15, wherein said transition metal chelator concentration is about 5 $\mu$M to about 40 mM.

17. The expanded hematopoietic cell population of claim 1, wherein said seeded cells are enriched for non-differentiated, early progenitor hematopoietic cells.

18. The expanded hematopoietic cell population of claim 1, wherein said seeded cells are enriched for $CD_{34}^+$ hematopoietic cells.

* * * * *

UNITED STATES PATENT AND TRADEMARK OFFICE
CERTIFICATE OF CORRECTION

PATENT NO. : 6,887,704 B2  Page 1 of 1
DATED : May 3, 2005
INVENTOR(S) : Tony Peled, Eitan Fibach and Avi Treves It is certified that error appears in the above-identified patent and that said Letters Patent is hereby corrected as shown below:

<u>Column 42,</u>
Line 48, "having reduced intracellular cooper content" should read -- having a reduced intracellular copper content --.

Signed and Sealed this

Twenty-eighth Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,887,704 B2  
APPLICATION NO. : 09/986897  
DATED : May 3, 2005  
INVENTOR(S) : Tony Peled, Eitan Fibach and Avi Treves Page 1 of 1

It is certified that error appears in the above-identified patent and that said Letters Patent is hereby corrected as shown below:

In the Related U.S. Application Data section Item (63), On the title page, "Continuation of application No. 09/463,320, filed as application No. PCT/IL99/00444 on Aug. 17, 1999" should read -- Continuation of U.S. patent application Ser. No. 09/463,320, filed Jan. 22, 2000, now U.S. Patent No. 6,962,698, which is a 35 USC 371 filing of PCT/IL99/00444, filed Aug. 17, 1999, which is a continuation-in-part of U.S. patent application Ser. No. 09/161,659, filed Sep. 29, 1998, now abandoned, which is a continuation-in-part of U.S. patent application Ser. No. 09/130,367, filed Aug. 7, 1998, now abandoned, which is a continuation-in-part of U.S. patent application Ser. No. 09/024,195, filed Feb. 17, 1998, now abandoned. PCT/IL99/00444 is a continuation-in-part of PCT/US99/02664, filed Feb. 8, 1999, which is a continuation of U.S. patent application Ser. No. 09/024,195, now abandoned and continuation-in-part of U.S. patent application Ser. NO.09/130,367, now abandoned. --.

Signed and Sealed this

Fifteenth Day of August, 2006

JON W. DUDAS  
*Director of the United States Patent and Trademark Office*